US006207668B1

(12) United States Patent
Braun et al.

(10) Patent No.: US 6,207,668 B1
(45) Date of Patent: Mar. 27, 2001

(54) SUBSTITUTED PYRIDINES/PYRIMIDINES, THEIR PREPARATION, AND THEIR USE AS PESTICIDES

(75) Inventors: Ralf Braun, Dernbach; Wolfgang Schaper, Diedorf; Werner Knauf, Liederbach; Ulrich Sanft, Hofheim; Manfred Kern, Lörzweiler; Werner Bonin, Kelkheim, all of (DE)

(73) Assignee: Hoechst Schering, Berlin (DE)

( * ) Notice: Subject to any disclaimer, the term of this patent is extended or adjusted under 35 U.S.C. 154(b) by 0 days.

(21) Appl. No.: 08/829,841

(22) Filed: Apr. 1, 1997

(30) Foreign Application Priority Data

Apr. 3, 1996 (DE) ................................................ 196 13 329

(51) Int. Cl.[7] .......................... A01N 43/54; C07D 405/12
(52) U.S. Cl. .......................... 514/256; 514/258; 514/259; 514/269; 514/212.02; 514/183; 540/466; 540/543; 540/453; 540/503; 540/293; 540/287; 540/288; 540/284; 540/280; 540/279; 540/278; 540/326; 540/327; 540/328; 540/329; 540/319; 540/256; 540/230; 540/334
(58) Field of Search .................................... 544/293, 287, 544/288, 284, 280, 279, 278, 326, 327, 328, 329, 319, 230; 514/256, 258, 259, 269, 212.02, 183; 540/466, 503

(56) References Cited

U.S. PATENT DOCUMENTS

| 5,280,009 | 1/1994 | Hamprechy | 504/239 |
| 5,571,815 | 11/1996 | Schaper et al. | 514/269 |

FOREIGN PATENT DOCUMENTS

| 0523533 | 1/1993 | (EP) . |
| WO 93/19050 | 9/1993 | (WO) . |
| WO 95/35293 | 12/1995 | (WO) . |

OTHER PUBLICATIONS

J. Med. Chem. 1981, 24, pp. 127–140, XP002033814, by Elslager et al.
Webber, Chemical Abstracts 92:35997 (1980) See Structure p. 34 of CA Printout.*
Cox et al Chemical Abstracts 87: 128906 (1977).*
Ahn et al, Chemical Abstracts, 125: 142765 (1996).*
Ahn et al, Chemical Abstracts, vol. 125, entry 142765 (1996).*
Webber Chemical Abstracts, vol. 92, entry 35997 (1980).*
Cox et al Chemical Abstracts, vol. 87, entry 128906 (1977).*
Mead Johnson, Chemical Abstracts, vol. 63, entry 1805 (h) (1965).*

* cited by examiner

Primary Examiner—John M Ford
(74) Attorney, Agent, or Firm—Frommer Lawrence & Haug LLP

(57) ABSTRACT

The present invention relates to novel substituted pyridines/pyrimidines of the formula I

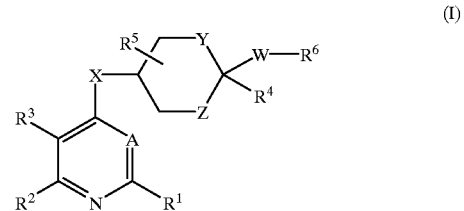

(I)

where A is CH or N; X is NH, oxygen or $S(O)_q$ where q is 0, 1 or 2; Y is a direct bond or $CH_2$; Z is oxygen, $NR^7$ or $S(O)_m$ is 0, 1 or 2, and the radicals $R^1$, $R^2$, $R^3$, $R^4$, $R^5$, $R^6$ and $R^7$ are as defined in the description, to processes for their preparation, and to their use as pesticides, fungicides, ovicides or as veterinary medicaments.

11 Claims, No Drawings

SUBSTITUTED PYRIDINES/PYRIMIDINES, THEIR PREPARATION, AND THEIR USE AS PESTICIDES

The invention relates to novel substituted pyridines/pyrimidines, to processes for their preparation and to their use as pesticides, fungicides and ovicides.

It has already been disclosed that certain cycloalkylamino- and -alkoxy-heterocycles have a fungicidal, acaricidal and insectidal action (U.S. Pat. No. 5,571,825). However, the biological activity of these compound is not satisfactory in all respects, in particular when low rates and concentrations are applied.

There have been found novel substituted pyridines/pyrimidines of the formula I

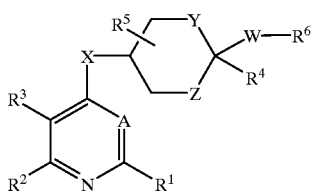

where the radicals and groups are as defined below and which are highly suitable for controlling animal pests such as insects, arachnids, nematodes, helminths and mollusks and their eggs, for controlling endo- and ectoparasites in the veterinary medicine sector and for controlling harmful fungi while having good plant tolerance and favorable toxicity to warm-blooded species.

The invention therefore relates to compounds of the formula I in which $R^1$ is hydrogen, halogen, $(C_1-C_4)$-alkyl, $(C_1-C_4)$-haloalkyl or $(C_3-C_5)$-cycloalkyl;

$R^2$ and $R^3$ independently of one another are hydrogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, tri-$(C_1-C_4)$-alkylsilyl-$(C_2-C_4)$-alkynyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_1-C_4)$-alkoxy-$(C_1-C_4)$-haloalkyl, $(C_1-C_4)$-haloalkoxy-$(C_1-C_4)$-haloalkyl, halogen, hydroxyl, $(C_1-C_4)$-hydroxyalkyl, $(C_1-C_4)$-alkanoyl, $(C_1-C_4)$-alkanoyl-$(C_1-C_4)$-alkyl, $(C_2-C_4)$-haloalkanoyl, $(C_3-C_5)$-cycloalkyl, $(C_3-C_5)$-halocycloalkyl, $(C_4-C_5)$-cyCloalkenyl, $(C_4-C_5)$-halocycloalkenyl, $(C_3-C_5)$ cycloalkoxy, cyano, cyan-$(C_1-C_4)$-alkyl, nitro, nitro-$(C_1-C_4)$-alkyl, thiocyano, thiocyano-$(C_1-C_4)$-alkyl, $(C_1-C_4)$-alkoxycarbonyl, $(C_1-C_4)$-alkoxycarbonyl-$(C_1-C_4)$-alkyl, $(C_1-C_4)$-haloalkoxycarbonyl, $(C_1-C_4)$-alkylthio, $(C_1-C_4)$-haloalkylthio, $(C_1-C_4)$-alkylthio-$C_1-C_4)$-alkyl, $(C_1-C_4)$-haloalkylthio-$(C_1-C_4)$-alkyl, $(C_1-C_4)$-alkylthio-$(C_1-C_4)$-haloalkyl, $(C_1-C_4)$-alkylsulfinyl, $(C_1-C_4)$-haloalkylsulfinyl, $(C_1-C_4)$-alkylsulfonyl, $(C_1-c_4)$-haloalkylsulfonyl; or $R^2$ and $R^3$ together with the carbon atoms to which they are bonded form an unsaturated 5- or 6-membered carbocyclic ring which, if it is a 5-membered ring, can contain an oxygen or sulfur atom instead of $CH_2$ or which, if it is a 6-membered ring, can contain one or two nitrogen atoms instead of one or two CH units and which is optionally substituted by 1, 2 or 3 identical or different radicals and these radicals being $(C_1-C_4)$-alkyl, $(C_1-C_4)$-haloalkyl, preferably trifluoromethyl, halogen, $(C_1-C_4)$-alkoxy or $(C_1-C_4)$-haloalkoxy; or $R^2$ and $R^3$ together with the carbon atoms to which they are bonded form a saturated 5-, 6- or 7-membered carbocyclic ring which can contain oxygen and/or sulfur instead of one or two $CH_2$-groups and which is optionally substituted by 1, 2 or 3 $(C_1-C_4)$-alkyl groups;

A is CH or N;

X is NH, oxygen or $S(O)_q$ where q=0, 1 or 2;

Y is a direct bond or $CH_2$;

Z is oxygen, $NR^7$, $S(O)_m$ where m=0, 1 or 2;

$R^4, R^5$ and $W-R^6$ are substituents of the heteroaliphatic ring system, where $R^4$ and $R^5$ independently of one another are hydrogen, halogen, cyano, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_3-C_6)$-cycloalkyl, $(C_4-C_6)$-cycloalkenyl, $(C_1-C_4)$-alkoxy, $(C_1-C_4)$-haloalkoxy, $(C_1-C_4)$-alkanoyloxy, $(C_1-C_4)$-haloalkanoyloxy, $(C_1-C_4)$-alkylthio or $(C_1-C_4)$-haloalkylthio;

W is a direct bond, oxygen, $—NR^{12}—$, $—CO—$, $—COO—$, $CONR^{12}—$, sulfur, $—C=N—$, $—C=N—O—$ or $—NR^{12}O—$;

$R^6$ is hydrogen, alkyl, alkenyl, alkynyl, cycloalkyl or cycloalkenyl and it being possible for one or more, preferably up to three, non-adjacent saturated carbon units in the last-mentioned 5 radicals to be replaced by a carbonyl group or by hetero atom units such as oxygen, $S(O)_x$ where x=0, 1 or 2, $NR^{13}$ or $SiR^{14}R^{15}$, and it being possible for these last-mentioned 5 radicals, with or without the abovementioned variations, optionally to be substituted by one or more, preferably up to three, in the case of fluorine up to the maximum number of, identical or different radicals $D^1R^{16}$, or $R^6$ can be aryl or heterocyclyl, it being possible for these two radicals to be unsubstituted or substituted by up to three, in the case of fluorine also up to the maximum number of, identical or different radicals $D^2R^{17}$, or $R^4$ and $R^6$ together form a three- to eight-membered ring system which is linked spirocyclically to the ring system which contains the hetero atoms Y and Z and in which one or two $CH_2$ groups, preferably one $CH_2$ group, can be replaced by hetero atom units such as oxygen, $S(O)_n$ where n=0, 1 or 2, or $NR^{18}$, where $R^7$ is hydrogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_1-C_4)$-alkoxy, $(C_1-C_4)$-alkanoyl, $(C_2-C_4)$-haloalkanoyl, $(C_1-C_4)$-alkoxy-$(C_1-C_4)$-alkyl, $(C_1-C_4)$-alkylthio-$(C_1-C_4)$-alkyl, $(C_1-C_4)$-alkoxycarbonyl, $(C_1-C_4)$-alkylsulfonyl, $(C_1-C_4)$-haloalkylsulfonyl, phenylcarbonyl, phenyl-$(C_1-C_4)$-alkyl or, if A is N, also phenyl, it being possible for the last-mentioned 3 radicals to be unsubstituted or to be substituted by up to three, in the case of fluorine also up to the maximum number of, identical or different substituents $R^{11}$, or $R^7$ is $CONR^8R^9$, in which $R^8$ and $R^9$ independently of one another are hydrogen, $(C_1-C_4)$-alkyl or phenyl, it being possible for the phenyl group to be unsubstituted or substituted by up to three, in the case of fluorine also up to the maximum number of, identical or different substituents $R^{10}$, and $R^{10}$ and $R^{11}$ independently of one another can be $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio or halogen;

$R^{12}$ is hydrogen, $(C_1-C_4)$-alkyl, $(C_1-C_4)$-alkanoyl or $(C_3-C_5)$-cycloalkyl;

$R^{13}$ is hydrogen, $(C_1-C_4)$-alkyl, $(C_1-C_4)$-alkoxy or $(C_1-C_4)$-alkanoyl;

$R^{14}$ and $R^{15}$ independently of one another are $(C_1-C_4)$-alkyl, preferably methyl;

$R^{18}$ is hydrogen, alkyl, alkanoyl, alkoxy, benzoyl, aryl or heteroaryl, it being possible for the last-mentioned 3 radicals to be unsubstituted or to be provided with up to three, in the case of fluorine also up to the maximum number of, identical or different substituents $R^{19}$;

$R^{19}$ can be $(C_1-C_4)$-alkyl, $(C_1-C_4)$-haloalkyl, $(C_1-C_4)$-alkoxy, $(C_1-C_4)$-haloalkoxy, cyano, nitro or halogen, and the ring system formed by $R^4$ and $R^6$ can be unsubstituted or provided with up to three substituents, but preferably one substituent, $D^3R^{20}$, or the ring system formed by $R^4$ and $R^6$ together with a further benzene ring or cydohexane ring forms a fused ring system, preferably the indane, 1,2,3,4-tetrahydronaphthalene, decalin or benzocycloheptane system, and the benzene ring in these fused systems can be unsubstituted or provided with up to three, in the case of fluorine also up to the maximum number of, identical or different substituents $D^4R^{21}$, where $D^1$, $D^2$, $D^3$ and $D^4$ are in each case independent of one another and are a direct bond, oxygen, $S(O)_k$, $SO_2O$, $OSO_2$, CO, OCO, COO, $SO_2NR^{22}$, $NR^{22}SO_2$, $NR^{22}O$, $ONR^{22}$, $NR^{22}$, $NR^{22}CO$, $CONR^{22}$ or $SiR^{23}R^{24}$, where k is 0, 1 or 2; and $R^{16}$, $R^{17}$, $R^{20}$ and $R^{21}$ in each case independently of one another are hydrogen, cyano, nitro, halogen, $(C_1-C_8)$-alkyl, $(C_1-C_8)$-haloalkyl, $(C_2-C_8)$-alkenyl, $(C_2-C_8)$-haloalkenyl, $(C_2-C_8)$alkynyl, $(C_2-C_8)$-haloalkynyl, $(C_1-C_8)$-alkoxy $(C_1-C_4)$-alkyl, $(C_1-C_8)$-haloalkoxy $(C_1-C_4)$-alkyl, $(C_1-C_8)$-alkylthio$(C_1-C_4)$-alkyl, $(C_1-C_8)$-haloalkylthio$(C_1-C_4)$-alkyl, $(C_3-C_8)$-cycloalkyl, $(C_4-C_8)$cycloalkenyl, $(C_3-C_8)$-cycloalkyl-$(C_1-C_4)$-alkyl, $(C_4-C_8)$-cycloalkenyl-$(C_1-C_4)$-alkyl, aryl, heterocyclyl, aryl-$(C_1-C_4)$-alkyl or heterocyclyl-$(C_1-C_4)$-alkyl, it being possible for the cycloaliphatic, aromatic or heterocyclic ring systems in the last-mentioned 8 radicals to be unsubstituted or to be provided by up to three, in the case of fluorine also up to the maximum number of, identical or different substituents $R^{25}$, where $R^{22}$ radicals independently of one another are hydrogen, $(C_1-C_4)$-alkyl, $(C_1-C_4)$-alkanoyl or $(C_3-C_5)$-cycloalkyl and $R^{23}$ and $R^{24}$ independently of one another are $(C_1-C_4)$-alkyl and $R^{25}$ radicals independently of one another are $(C_1-C_4)$-alkyl, $(C_1-C_4)$-haloalkyl, $(C_1-C_4)$-alkoxy, $(C_1-C_4)$-haloalkoxy, cyano, nitro, halogen, $(C_1-C_4)$-alkanoyl or $(C_2-C_4)$-haloalkanoyl, or two of the radicals $R^{16}$, $R^{17}$, $R^{20}$, $R^{21}$, $R^{25}$ on the same carbon atom together and in each case independently of one another are an oxo group;

and salts thereof, preferably acid addition salts.

Preferred are those compounds of the formula I where $R^6$ is hydrogen, $(C_1-C_{20})$-alkyl, $(C_2-C_{20})$-alkenyl, $(C_2-C_{20})$-alkynyl, $(C_3-C_8)$-cycloalkyl or $(C_4-C_8)$-cycloalkenyl and one or more, preferably up to three, non-adjacent saturated carbon units in the last-mentioned 5 radicals can be replaced by a carbonyl group or by hetero atom units such as oxygen, $S(O)_x$ where x=0, 1 or 2, $NR^{13}$ or $SiR^{14}R^{15}$, and where these last-mentioned 5 radicals, with or without the above-mentioned variations, can optionally be substituted by one or more, preferably up to three, in the case of fluorine up to the maximum number of, identical or different radicals $D^1R^{16}$, or $R^6$ can be aryl or heterocyclyl, it being possible for these two radicals to be unsubstituted or substituted by up to three, in the case of fluorine also up to the maximum number of identical or different radicals $D^2R^{17}$, or $R^4$ and $R^6$ together form a three- to eight-membered ring system which is spirocyclically linked with the ring system containing the hetero atoms Y and Z and in which one or two $CH_2$ groups, preferably one $CH_2$ group, can be replaced by hetero atom units such as oxygen, $S(O)_n$ where n=0, 1 or 2 or $NR^{18}$, where $R^{13}$ is hydrogen, $(C_1-C_4)$-alkyl, $(C_1-C_4)$-alkoxy or $(C_1-C_4)$-alkanoyl;

$R^{14}$ and $R^{15}$ independently of one another are $(C_1-C_4)$-alkyl, preferably methyl;

$R^{18}$ is hydrogen, $(C_1-C_8)$-alkyl, $(C_1-C_8)$-alkanoyl, $(C_1-C_8)$-alkoxy, benzoyl, aryl or heteroaryl, it being possible for the last-mentioned 3 radicals to be unsubstituted or to be provided with up to three, in the case of fluorine also up to the maximum number of, identical or different substituents $R^{19}$;

$R^{19}$ can be $(C_1-C_4)$-alkyl, $(C_1-C_4)$-haloalkyl, $(C_1-C_4)$-alkoxy, $(C_1-C_4)$-haloalkoxy, cyano, nitro or halogen, and the ring system formed by $R^4$ and $R^6$ can be unsubstituted or provided with up to three substituents, but preferably one substituent, $D^3R^{20}$, or the ring system formed by $R^4$ and $R^6$ together with a further benzene ring or cyclohexane ring together forms a fused ring system, preferably the indane, 1,2,3,4-tetrahydronaphthalene, decalin or benzocycloheptane system, and the benzene ring in these fused systems can be unsubstituted or provided with up to three, in the case of fluorine also up to the maximum number of, identical or different substituents $D^4R^{21}$, where, amongst the compounds for which the carbon atom between Y and Z only has attached to it the substituent $W-R^6$, the substituents X and $W-R^6$ are preferably in the cis-position relative to each other;

$D^1$, $D^2$, $D^3$ and $D^4$ are in each case independent of one another and are a direct bond, oxygen, $S(O)_k$, $SO_2O$, $OSO_2$, CO, OCO, COO, $SO_2NR^{22}$, $NR^{22}SO_2$, $ONR^{22}$, $NR^{22}O$, $SIR^{23}O$, $NR^{22}CO$, $CONR^{22}$ or $SiR^{23}R^{24}$, where k is 0, 1 or 2; and $R^{16}$, $R^{17}$, $R^{20}$ and $R^{21}$ in each case independently of one another are hydrogen, cyano, nitro, halogen, $(C_1-C_8)$-alkyl, $(C_1-C_8)$-haloalkyl, $(C_2-C_8)$-alkenyl, $(C_2-C_8)$-haloalkenyl, $(C_2-C_8)$alkynyl, $(C_2-C_8)$-haloalkynyl, $(C_1-C_8)$-alkoxy $(C_1-C_4)$-alkyl, $(C_1-C_8)$-haloalkoxy $(C_1-C_4)$-alkyl, $(C_1-C_8)$-alkylthio$(C_1-C_4)$-alkyl, $(C_1-C_8)$-haloalkylthio$(C_1-C_4)$-alkyl, $(C_3-C_8)$-cycloalkyl, $(C_4-C_8)$-cycloalkenyl, $(C_3-C_8)$-cycloalkyl-$(C_1-C_4)$-alkyl, $(C_4-C_8)$-cycloalkenyl-$(C_1-C_4)$-alkyl, aryl, heterocyclyl, aryl-$(C_1-C_4)$-alkyl or heterocyclyl-$(C_1-C_4)$-alkyl, it being possible for the cycloaliphatic, aromatic or heterocyclic ring systems in the last-mentioned 8 radicals to be unsubstituted or to be provided by up to three, in the case of fluorine also up to the maximum number of, identical or different substituents $R^{25}$, where $R^{22}$ radicals independently of one another are hydrogen, $(C_1-C_4)$-alkyl, $(C_1-C_4)$-alkanoyl or $(C_3-C_5)$-cycloalkyl and $R^{23}$ and $R^{24}$ independently of one another are $(C_1-C_4)$-alkyl and $R^{25}$ radicals independently of one another are $(C_1-C_4)$-alkyl, $(C_1-C_4)$-haloalkyl, $(C_1-C_4)$-alkoxy, $(C_1-C_4)$-haloalkoxy, cyano, nitro, halogen, $(C_1-C_4)$-alkanoyl or $(C_2-C_4)$-haloalkanoyl, or two of the radicals $R^{16}$, $R^{17}$, $R^{20}$, $R^{21}$, $R^{25}$ on the same carbon atom together and in each case independently of one another are an oxo group;

in particular those compounds in which $R^6$ is hydrogen, $(C_1-C_8)$-alkyl, $(C_2-C_8)$-alkenyl, $(C_2-C_8)$-alkynyl, $(C_3-C_8)$-cycloalkyl or $(C_4-C_8)$-cycloalkenyl and one or more, preferably up to three, non-adjacent saturated carbon units in the last-mentioned 5 radicals can be replaced by a carbonyl group or by hetero atom units such as oxygen, $S(O)_x$ where x=0, 1 or 2, $NR^{13}$ or $SiR^{14}R^{15}$, and where these last-mentioned 5 radicals, with or without the above-mentioned variations, can optionally be substituted by one or more, preferably up to three, in the case of fluorine up to the maximum number of, identical or different radicals $D^1R^{16}$, or $R^6$ can be aryl or heterocyclyl, it being possible for these two radicals to be unsubstituted or substituted by up to three, in the case of fluorine also up to the maximum number of identical or different radicals $D^2R^{17}$, or $R^4$ and $R^6$ together form a five- or six-membered ring system which is preferably spirocyclically linked to the ring system which contains the hetero atoms Y and Z and in which a $CH_2$ group can be replaced by hetero atom units such as oxygen, $S(O)_n$ where n=0, 1 or 2 or $NR^{18}$, where $R^{13}$ is hydrogen, $(C_1-C_4)$-alkyl, $(C_1-C_4)$-alkoxy or $(C_1-C_4)$-alkanoyl and $R^{14}$ and $R^{15}$ independently of one another are $(C_1-C_4)$-alkyl, preferably methyl, $R^{18}$ is hydrogen, $(C_1-C_8)$-alkyl, $(C_1-C_8)$-alkanoyl, benzoyl, aryl or heteroaryl, it being possible for the last-mentioned 3 radicals to be unsubstituted or to be provided with up to three, in the case of fluorine also up to the maximum number of, identical or different substituents $R^{19}$ and $R^{19}$ can be $(C_1-C_4)$-alkyl, $(C_1-C_4)$-haloalkyl, $(C_1-C_4)$-alkoxy, $(C_1-C_4)$-haloalkoxy, cyano, nitro or halogen and the ring system formed by $R^4$ and $R^6$ can be unsubstituted or provided with up to three substituents, but preferably one substituent, $D^3R^{20}$, or the ring system formed by $R^4$ and $R^6$ together forms a fused ring system, preferably the indane, 1,2,3,4-tetrahydronaphthalene, decalin or benzocycloheptane system, and the benzene ring in these fused systems can be unsubstituted or provided with up to three, in the case of fluorine also up to the maximum number of, identical or different substituents $D^4R^{21}$, where, amongst the compounds for which the carbon atom between Y and Z where Y=$CH_2$ only has attached to it the substituent W-$R^6$, the substituents X and W-$R^6$ are in the cis-position relative to each other;

$D^1$, $D^2$, $D^3$ and $D^4$ are in each case independent of one another and are a direct bond, oxygen, $S(O)_k$, $SO_2O$, $OSO_2$, CO, OCO, COO, $SO_2NR^{22}$, $NR^{22}SO_2$, $NR^{22}O$, $ONR^{22}$, $NR^{22}$, $NR^{22}CO$, or $CONR^{22}$, where k is 0, 1 or 2; and $R^{22}$ radicals independently of one another are hydrogen, $(C_1-C_4)$-alkyl, $(C_1-C_4)$-alkanoyl or $(C_3-C_5)$-cycloalkyl, and where $R^{16}$, $R^{17}$, $R^{20}$ and $R^{21}$ in each case independently of one another are hydrogen, cyano, nitro, halogen, preferably fluorine, $(C_1-C_8)$-alkyl, $(C_3-C_8)$-cycloalkyl, aryl or heterocyclyl, where the cycloaliphatic, aromatic or heterocyclic ring systems in the last-mentinoed 3 radicals can be unsubstituted or provided with up to three, in the case of fluorine also up to the maximum number of, identical or different substitutents $R^{25}$, where $R^{25}$ radicals independently of one another can be $(C_1-C_4)$-alkyl, $(C_1-C_4)$-haloalkyl, $(C_1-C_4)$-alkoxy, $(C_1-C_4)$-haloalkoxy, cyano, nitro, halogen, or two of the radicals $R^{16}$, $R^{17}$, $R^{20}$, $R^{21}$, and $R^{25}$ on the same carbon atom together and in each case independently of one another are an oxo group;

especially preferred are those compounds of the formula I where $R^6$ is $(C_1-C_8)$-alkyl in which one of more, preferably up to three, non-adjacent saturated carbon units can be replaced by oxygen and which, with or without the abovementioned variations, can optionally be substituted by one or more, preferably up to three, in the case of fluorine up to the maximum number of, identical or different radicals $D^1R^{20}$, or $R^6$ can be aryl or heterocyclyl, it being possible for these two radicals to be unsubstituted or to be substituted by up to three, in the case of fluorine also up to the maximum number of, identical or different radicals $D^2R^{21}$.

Furthermore preferred compounds of the formula I are those in which $R^1$ is hydrogen, chlorine or fluorine, $R^2$ is $(C_1-C_4)$-alkyl, $(C_2-C_4)$-alkenyl, $(C_2-C_4)$-alkynyl, tri-$(C_1-C_4)$-alkylsilyl -$(C_2-C_4)$-alkynyl, $(C_1-C_4)$-haloalkyl, cyclopropyl, halocyclopropyl, methoxymethyl or cyano;

$R^3$ is hydrogen, halogen, methyl, ethyl, ethenyl, ethynyl, methoxy, ethoxy, cyano, trifluoromethyl, fluoromethylthio or methoxycarbonyl; or $R^2$ and $R^3$ together with the carbon atoms to which they are bonded form an optionally substituted unsaturated 5- or 6-membered carbocyclic ring which, if it is a 5-membered ring, can contain a sulfur atom instead of $CH_2$, or $R^2$ and $R^3$ together with the carbon atoms to which they are bonded form a saturated 5- or 6-membered ring which can contain oxygen or sulfur instead of a $CH_2$ group;

A is CH or N;

X is NH or oxygen;

Y is a direct bond or $CH_2$;

Z is oxygen, $NR^7$, $S(O)_m$ where m=0,1 or 2;

$R^4$ is hydrogen, $(C_1-C_4)$-alkyl, trifluoromethyl or $(C_1-C_4)$-alkoxy;

$R^5$ is hydrogen;

W is a direct bond, oxygen, —CO—, —COO—, $CONR^{12}$, sulfur, —C=N—, —C=N—O— and $R^{12}$ in this context can be hydrogen, $(C_1-C_4)$-alkyl, $(C_1-C_4)$-alkanoyl or $(C_3-C_5)$-cycloalkyl and $R^7$ is $(C_1-C_4)$-alkyl;

in particular those compounds in which $R^1$ is hydrogen, $R^2$ is methyl, ethyl, propyl, isopropyl, $(C_1-C_2)$-fluoroalkyl, cyclopropyl or methoxymethyl;

R³ is halogen, methyl, ethyl, ethenyl, ethynyl, methoxy, ethoxy, trifluoromethyl, fluoromethylthio, methoxycarbonyl or cyano; or R² and R³ together with the ring system to which they are bonded form the quinazoline or quinoline system which can be substituted by fluorine in the carbocyclic moiety; or R² and R³ together with the carbon atoms to which they are bonded form a saturated 6-membered ring which can contain an oxygen or sulfur atom instead of a $CH_2$ group;

R⁴ is hydrogen or methyl; and

R⁵ is hydrogen.

Particularly preferred compounds of the formula I are those where

R¹ is hydrogen;

R² is ethyl, propyl, isopropyl, 1-fluoroethyl or methoxymethyl;

R³ is fluorine, chlorine, bromine, cyano, ethenyl, ethynyl or methoxy; or, in the event that A is nitrogen, R² and R³ together with the ring system to which they are bonded form the quinazoline system which can be substituted by a fluorine atom;

R⁴ is hydrogen or methyl; and

R⁵ is hydrogen.

Most preferred are those compounds of the formula I in which

R¹ is hydrogen;

R² is ethyl or methoxymethyl;

R³ is fluorine, chlorine, bromine or methoxy; or

A is CH or N;

X is NH;

Z is oxygen and

R⁴ and R⁵ are hydrogen.

In the above formula, "halogen" is to be understood as meaning a fluorine, chlorine, bromine or iodine atom;

the term "$(C_1–C_4)$-alkyl" an unbranched or branched hydrocarbon radical having I to 4 carbon atoms such as, for example, the methyl, ethyl, propyl, isopropyl, 1-butyl, 2-butyl, 2-methylpropyl or tert-butyl radical;

the term "$(C_1–C_8)$-alkyl" the abovementioned alkyl radicals and also, for example, the pentyl, 2-methylbutyl, 1,1-dimethylpropyl, hexyl, heptyl, octyl, or 1,1,3,3-tetramethylbutyl radical;

the term "$(C_1–C_{20})$-alkyl" the abovementioned alkyl radicals and also, for example, the nonyl, 1-decyl, 2-decyl, undecyl, dodecyl, pentadecyl or eicosyl radical;

the term "$(C_1–C_4)$-haloalkyl" an alkyl group mentioned under the term "$(C_1–C_4)$-alkyl" in which one or more hydrogen atoms are replaced by halogen, preferably selected from amongst chlorine and fluorine, such as, for example, the trifluoromethyl group, the 1-fluoroethyl group, the 2-fluoroethyl group, the 2,2,2-trifluoroethyl group, the chloromethyl or fluoromethyl group, the difluoromethyl group or the 1,1,2,2-tetrafluoroethyl group;

the term "$(C_1–C_2)$-fluoroalkyl" for example, the mono-, di- and trifluoromethyl group, the 1-fluoroethyl, 2-fluoroethyl, 1,1-difluoroethyl, 2,2-difluoroethyl, 2,2,2-trifluoroethyl or a pentafluoroethyl group;

the term "cycloalkyl" preferably $(C_3–C_8)$-cycloalkyl;

the term "cycloalkenyl" preferably $(C_4–C_8)$-cloalkenyl;

the term "$(C_3–C_5)$-cycloalkyl" the cyclopropyl, cyclobutyl or cyclopentyl group;

the term "$(C_3–C_8)$-cycloalkyl" the radicals mentioned above under "$(C_3–C_5)$-cycloalkyl" and also the cyclohexyl, cycloheptyl or cyclooctyl radical, but also bicyclic systems such as, for example, the norbornyl group or the bicyclo[2.2.2]octane radical;

the term "$(C_3–C_5)$-halocycloalkyl" one of the abovementioned $(C_3–C_5)$-cycloalkyl radicals in which one or more hydrogen atoms are replaced by halogen, preferably selected from amongst chlorine and fluorine, such as, for example, the 2,2-difluoro- or 2,2-dichlorocyclopropane group or the fluorocyclopentane radical;

the term "$(C_2–C_4)$-alkenyl" for example the vinyl, allyl, 2-methyl-2-propenyl or 2-butenyl group;

the term "$(C_2–C_8)$-alkenyl" the abovementioned radicals and, for example, the 2-pentenyl or the 2-octenyl group;

the term "$(C_2–C_{20})$-alkenyl" the abovementioned radicals and also, for example, the 2-decenyl or the 2-eicosenyl group;

the term "$(C_2–C_4)$-haloalkenyl" a $(C_2–C_4)$-alkenyl group in which one or more hydrogen atoms are replaced by halogen, preferably selected from amongst chlorine and fluorine, the term "$(C_2–C_8)$-haloalkenyl" a $(C_2–C_8)$-alkenyl group in which one or more hydrogen atoms are replaced by halogen, preferably selected from amongst chlorine and fluorine;

the term "$(C_4–C_5)$-cycloalkenyl" the cyclobutenyl or cyclopentenyl group;

the term "$(C_4–C_8)$-cycloalkenyl" the abovementioned radicals and also, for example, the 2-cyclohexenyl or the 2-cyclopentenyl group;

the term "$(C_2–C_4)$-alkynyl", for example, the ethynyl, the propargyl, or the 1-butynyl, 2-butynyl or 3-butynyl group;

the term "$(C_2–C_8)$-alkynyl" the abovementioned radicals and also, for example, the 2-pentynyl or the 2-octynyl group, the term "$(C_2–C_{20})$-alkynyl" the abovementioned radicals and also, for example, the 2-decynyl group;

the term "$(C_2–C_4)$-haloalkynyl" a $(C_2–C_4)$-alkynyl group in which one or more hydrogen atoms are replaced by halogen, preferably selected from amongst chlorine and fluorine, or else the iodoethynyl group;

the term "$(C_2–C_8)$-haloalkynyl" a $(C_2–C_8)$-alkynyl group in which one or more hydrogen atoms are replaced by halogen, preferably selected from amongst chlorine and fluorine;

the term "tri-$(C_1–C_4)$-alkylsilyl-$(C_2–C_4)$-alkynyl" preferably the trimethylsilylethynyl group;

the term "$(C_1–C_4)$-hydroxyalkyl" for example the hydroxymethyl, 1-hydroxyethyl, 2-hydroxyethyl, 1-hydroxy-1methylethyl or the 1-hydroxypropyl group;

the term "$(C_1–C_4)$-alkanoyl" for example the formyl, acetyl, propionyl, 2-methylpropionyl or butyryl group;

the term "$(C_2–C_4)$-haloalkanoyl" a $(C_2–C_4)$-alkanoyl group in which one or more hydrogen atoms are replaced by halogen, preferably selected from amongst chlorine and fluorine;

the term "cyano-$(C_1–C_4)$-alkyl" a cyanoalkyl group whose hydrocarbon radical has the meanings given for the term "$(C_1–C_4)$-alkyl";

the term "$(C_1-C_4)$-alkoxycarbonyl" for example the methoxycarbonyl, ethoxycarbony, propoxycarbonyl, butoxycarbonyl or tert-butoxycarbonyl group;

the term "$(C_1-C_4)$-haloalkoxycarbonyl" a $(C_1-C_4)$-alkoxycarbonyl group in which one or more hydrogen atoms are replaced by halogen, preferably selected from amongst chlorine and fluorine;

the term "$(C_1-C_4)$-alkylthio" an alkylthio group whose hydrocarbon radical is as defined for the term "$(C_1-C_4)$-alkyl";

the term "$(C_1-C_4)$-haloalkylthio" a $(C_1-C_4)$-alkylthio group in which one or more hydrogen atoms are replaced by halogen, preferably selected from amongst chlorine and fluorine;

the term "fluoromethylthio" the mono-, di- and trifluoromethylthio group;

the term "$(C_1-C_4)$-alkylsulfinyl" for example the methyl-, ethyl-, propyl-, isopropyl-, butyl-, isobutyl-, sec-butyl- or tert-butylsulfinyl group;

the term "$(C_1-C_4)$-alkylsufonyl" for example the methyl-, ethyl-, propyl-, isopropyl-, butyl-, isobutyl-, sec-butyl- or tert-butylsulfonyl group;

the terms "$(C_1-C_4)$-haloalkylsulfinyl" and "$(C_1-C_4)$-haloalkylsulfonyl" $(C_1-C_4)$-alkylsulfinyl- and $(C_1-C_4)$-alkylsulfonyl radicals as defined above in which one or more hydrogen atoms are replaced by halogen, preferably selected from amongst chlorine and fluorine;

the term "$(C_1-C_4)$-alkoxy" an alkoxy group whose hydrocarbon radical is as defined for the term "$(C_1-C_4)$-alkyl";

the term "$(C_3-C_5)$-cycloalkoxy" for example the cyclopropoxy, cyclobutoxy or the cyclopentoxy group;

the term "$(C_1-C_4)$-haloalkoxy" a haloalkoxy group whose halohydrocarbon radical is as defined for the term "$(C_1-C_4)$-haloalkyl";

the term "$(C_1-C_4)$-alkoxy-$(C_1-C_4)$-alkyl" for example a 1-methoxyethyl group, a 2-methoxyethyl group, a 2-ethoxyethyl group, a methoxymethyl or ethoxymethyl group, a 3-methoxypropyl group or a 4-utoxybutyl group;

the terms "$(C_1-C_4)$-haloalkoxy-$(C_1-C_4)$-alkyl", "$(C_1-C_4)$-alkoxy-$(C_1-C_4)$-haloalkyl" and "$(C_1-C_4)$-haloalkoxy-$(C_1-C_4)$-haloalkyl" $(C_1-C_4)$-alkoxy-$(C_1-C_4)$-alkyl radicals as defined above in which one or more hydrogen atoms are replaced by halogen, preferably selected from amongst chlorine and fluorine;

the term "$(C_1-C_4)$-alkylthio-$(C_1-C_4)$-alkyl" for example methylthiomethyl, ethylthiomethyl, propylthiomethyl, 2-methylthioethyl, 2-ethylthioethyl or 3-methylthiopropyl;

the term "aryl" a carbocyclic aromatic radical having preferably 6 to 14, in particular 6 to 12, carbon atoms such as, for example, phenyl, naphthyl or biphenylyl, preferably phenyl;

the term "heterocyclyl" a heteroaromatic or heteroaliphatic ring system, "heteroaromatic ring system" to be understood as meaning an aryl radical in which at least one CH group is replaced by N and/or at least two adjacent CH groups are replaced by S, NH or O, for example a radical of thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-triazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine or 4H-quinolizine;

and the term "heteroaliphatic ring system" a $(C_3-C_8)$-cycloalkyl radical in which at least one carbon unit is replaced by O, S or a group $NR^{12}$ and $R^{12}$ is hydrogen, $(C_1-C_4)$-alkyl, $(C_1-C_4)$-alkoxy or aryl;

What has been explained above applies analogously to homologs or radicals derived therefrom.

The present invention relates to the compounds of the formula I in the form of the free basis or of an acid addition salt. Acids which can be used for salt formation are inorganic acids such as hydrochloric acid, hydrobromic acid, nitric acid, sulfuric acid, phosphoric acid, or organic acids such as formic acid, acetic acid, propionic acid, malonic acid, oxalic acid, fumaric acid, adipic acid, stearic acid, oleic acid, methanesulfonic acid, benzenesuffonic acid or toluenesulfonic acid.

Beside the abovementioned cis/trans isomerism on the hetero-cycloalkyl group, some of the compounds of the formula I have one or more symmetric carbon atoms or stereoisomers on double bonds. Enantiomers or diastereomers are therefore possible. The scope of the invention extends to the pure isomers and also to mixtures of these. The diastereomer mixtures can be separated into the components by customary methods, for example by selective crystallization from suitable solvents or by chromatography. Racemates can be resolved by customary methods to give the enantiomers, for example by salt formation with an optically active acid, separation of the diastereomeric salts and liberation of the pure enantiomers by means of a base.

The invention furthermore relates to a process for the preparation of compounds of the formula I which comprises reacting a compound of the formula II

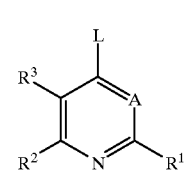

(II)

where A, $R^1$, $R^2$ and $R^3$ are as defined for formula I and L is a leaving group, for example halogen, alkylthio, alkanesulfonyloxy or arylsulfonyloxy, alkylsulfonyl or arylsulfonyl, with a nucleophile of the formula III

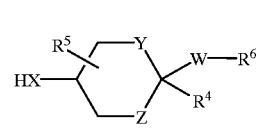

(III)

where W, X, Y, Z, $R^4$, $R^5$ and $R^6$ are as defined above for formula I and, if appropriate, further derivatizing the nitrogen heterocycle or the side chain $R^6$ in the compounds of the formula I obtained in the above or any other manner.

The above-described substitution reaction is known in principle. The leaving group L can be varied within wide limits and can be, for example, a halogen atom such as fluorine, chlorine, bromine or iodine, or alkylthio such as methyl- or ethylthio, or alkanesulfonyloxy such as methane-, trifluoromethane- or ethanesulfonyloxy or arylsulfonyloxy, such as benzenesulfonyloxy or toluenesulfonyloxy, or alkyl sulfonyloxy such as methyl- or ethylsulfonyl, or arylsulfonyl such as phenyl- or toluenesulfonyl.

The abovementioned reaction was carried out in a termperature range of from 20 to 1 50° C., expediently in the presence of a base and, if appropriate, in an inert organic solvent such as, for example, N,N-dimethylformamide, N,N-dimethylacetamide, dimethyl sulfoxide, N-methylpyrrolidin-2-one, dioxane, tetrahydrofuran, 4-methyl-2-pentanone, methanol, ethanol, butanol, ethylene glycol, ethylene glycol dimethyl ether, toluene, chlorobenzene or xylene. Mixtures of the abovementioned solvents can also be used.

In the event that X is oxygen, examples of suitable bases are alkali metal carbonates, alkali metal hydrogen carbonates, alkali metal amides, alkali metal hydrides, alkaline earth metal carbonates, alkaline earth metal hydrogen carbonates, alkaline earth metal amides or alkaline earth metal hydrides such as sodium carbonate, sodium hydrogen carbonate, potassium carbonate, sodium amide or sodium hydride, and in the event that X is NH, examples of suitable bases are alkali metal carbonates, alkali metal hydrogen carbonates, alkali metal hydroxides, alkali metal amides, alkali metal hydrides, alkaline earth metal carbonates, alkaline earth metal hydrogen carbonates, alkaline earth metal hydroxides, alkaline earth metal amides or alkaline earth metal hydrides such as sodium carbonate, sodium hydrogen carbonate, potassium carbonate, sodium hydroxide, sodium amide or sodium hydride or organic bases such as triethylamine or pyridine. A second equivalent of an amine of the formula III can also be employed as auxiliary base.

Most of the compounds of the formula II which are required as starting materials are known from the literature or can be prepared analogously to known methods (cf. EP 370 391, EP 470 600, DOS 43 31 179, DOS 44 04 702.)

To prepare the nucleophiles of the formula III, suitably substituted cations of the formula IV are used as starting materials and are converted into the corresponding amines by reductive amination ($H_2$, $NH_3$, metal catalyst or ammonium acetatesodium cyanoborohydride or Leuckart-Wallach reduction) or into the corresponding alcohols by reduction with a complex metal hydride.

Furthermore, the nucleophiles of the formula III where X=NH can be prepared by reducing an oxime or imine or by subjecting an alkyl halide or alkyl tosylate by a Gabriel reaction or a Mitsunobu reaction with phthalimide and subsequent hydrazinolysis. Equally, these nucleophiles can be synthesized by reacting an alkyl halide or alkyl tosylate with a metal azide and reducing the azide with a suitable reducing agent, for example a complex metal hydride, hydrogen in the presence of a hydrogenation catalyst or phosphine or phosphite. The alkyl halides or alkyl tosylates are accessible from the alcohols of formula V.

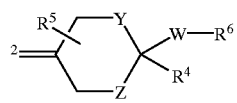

formula IV $X^2 = O$

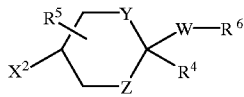

formula V $X^2 = H$ or OH are commercially available

The ketones of the formula IV or the alcohols of the formula V are known from the literature or can be synthesized analogously to known processes (cf. M. A. Gianturco, P. Friedel, A. S. Giammarino, Tetrahedron 1964, 20, 1763. U.S. Pat. No. 4,388,104. Y. Senda, T. Terasawa, I. lshiyama, S. Kamiyama, S. Imaizumi, Bull. Chem. Soc. Jpn. 1989, 62, 2948.

D. N. Reinhardt, W. P. Trompenaars, I. Geevers, Synthesis 1976, 368.

Curtis W. Smith, D. G. Norton, S. A. Ballard, J. Am. Chem. Soc. 1951, 73, 5267).

The active substances are well tolerated by plants and have a favorable toxicity to warm-blooded species and are suitable for controlling animal pests, in particular insects, arachnids, helminths and molluscs and their eggs, very especially preferably for controlling insects and arachnids found in agriculture, in livestock breeding, in forests, in the protection of stored products and materials and in the hygiene sector. They are effective against normally sensitive and resistant species and all or some developmental stages. The abovementioned pests include: From the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., lxodes spp., Psoroptes spp., Chorioptes spp., Sarcoptes spp., Tarsonemus spp., *Bryobia praetiosa,* Panonychus spp., Tetranychus spp., Eotetranychus spp., Oligonychus spp., Eutetranychus spp.

From the order of the Isopoda, for example, *Oniscus asselus, Armadium vulgar, Porcelio scaber.*

From the order of the Diplopoda, for example, *Blaniulus guttulatus.*

From the order of the Chilopoda, for example, *Geophilus carpophagus,* Scutigera spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea madeirae, Blatella germanica, Acheta domesticus,* Gryllotalpa spp., *Locusta migratoria migratorioides, Melanoplus differentialis, Schistocerca gregaria.*

From the order of the Isoptera, for example, Reticulitermes spp.

From the order of the Anoplura, for example, *Phylloera vastatrix,* Pemphigus spp., *Pediculus humanus corporis,* Haematopinus spp., Linognathus spp.

From the order of the Mallophaga, for example, Trichodectes pp., Damalinea spp.

From the order of the Thysanoptera, for example, *Hercinothrips femoralis, Thrips tabaci.*

From the order of the Heteroptera, for example, Eurygaster spp., *Dysdercus intermedius, Piesma quadrata, Cimex lectularius, Rhodnius prolixus,* Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Eusceius bilobatus, Nephotettix cincticeps, Lecanium corni, Saissetia oleae, Laodelphax striatellus, Nilaparvata lugens, Aonidiella aurantii, Aspidiotus hederae,* Pseudococcus spp., Psylia spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima, Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylloides chrysocephala, Epilachna varivestis,* Atomaria spp., *Oryzaephilus surinamensis,* Anthonumus spp., Sitophilus spp., *Otiorrhynchus sulcatus, Cosmopolites sordidus, Ceuthorrynchus assimilis, Hypera postica,* Dermestes spp., Trogoderma, Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis, Costelytra zealandica.*

From the order of the Hymenoptera, for example, Diprion spp., Hoplocampa spp., Lasius spp., *Monomorium pharaonis,* Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinelia frit,* Phorbia spp., *Pegomyia hyoscyami, Ceratitis capitata, Dacus oleae, Tipula paludosa.*

From the order of the Siphonaptera, for example, *Xenopsylla cheopsis,* Ceratophyllus spp.

From the order of the Arachnida, for example, *Scorpio maurus, Latrodectus mactans.*

From the class of the helminths, for example, Haemonchus, Trichostrongulus, Ostertagia, Cooperia, Chabertia, Strongyloides, Oesophagostomum, Hyostrongulus, Ancylostoma, Ascaris and Heterakis and also Fasciola.

From the class of the gastropods, for example, Deroceras spp., Arion spp., Lymnaea spp., Galba spp., Succinea spp., Biomphalaria spp., Bulinus spp., Oncomelania spp.

From the class of the bivalves, for example, Dreissena spp.

The plant-parasitic nematodes which can be controlled according to the invention include, for example, the root-parasitic soil nematodes such as, for example, those from the genera Meloidogyne (root-knot nematodes, such as *Meloidogyne incognita, Meloidogyne hapla* and *Meloidogyne javanica*), Heterodera and Globodera (cyst-forming nematodes, such as *Globodera rostochiensis, Globodera pallida, Heterodera trifolii*) and from the genera Radopholus, such as *Radopholus similis,* Pratylenchus, such as *Pratylenchus neglectus, Pratylenchus penetrans* and *Pratylenchus curvitatus;*

Tylenchulus, such as *Tylenchulus semipenetrans,* Tylenchorhynchus, such as *Tylenchorhynchus dubius* and *Tylenchorhynchus claytoni,* Rotylenchus, such as *Rotylenchus robustus,* Heliocotylenchus, such as *Haliocotylenchus multicinctus,* Belonoaimus, such as *Belonoaimus longicaudatus,* Longidorus, such as *Longidorus elongatus,* Trichodorus, such as *Trichodorus primitivus* and Xiphinema, such as *Xiphinema index.*

Furthermore, the compounds according to the invention can be used for controlling the nematode genera Ditylenchus (stem parasites, such as *Ditylenchus dipsaci* and *Ditylenchus destructor*), Aphelenchoides (foliar nematodes, such as *Aphelenchoides ritzemabosi*) and Anguina (seed nematodes, such as *Anguina tritici*).

The invention also relates to compositions, in particular to insecticidal, acaricidal and ovicidal compositions, which comprise the compounds of the formula I in addition to suitable formulation auxiliaries.

The compositions according to the invention comprise the active ingredients of the formula I in a concentration range of from 0.00000001 to 95% by weight, preferably from 1 to 95% by weight.

They can be formulated in various ways, depending on the prevailing biological and/or chemico-physical parameters. The following formulations are therefore possible:

Wettable powders (WP), emulsifiable concentrates (EC), aqueous solutions (SL), emulsions, sprayable solutions, oil- or water-based dispersions (SC), suspoemulsions (SE), dusts (DP), seed-treatment products, granules in the form of microgranules, spray granules, coated granules and adsorption granules, water-dispersible granules (WG), ULV formulations, microcapsules, waxes or baits.

These individual types of formulation are known in principle and are described, for example, in:

Winnacker-Kuchler, "Chemische Technologie" [Chemical Engineering], Volume 7, C. Hauser Verlag Munich, 4th Ed. 1986; van Falkenberg, "Pesticides Formulations", Marcel Dekker N.Y., 2nd Ed. 1972–73; K. Martens, "Spray Drying Handbook", 3rd Ed. 1979, G. Goodwin Ltd. London.

The formulation auxiliaries required, such as inert materials, surfactants, solvents and other additives are also known and are described, for example, in:

Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1967; Winnacker-Küchler, "Chemische Technologie" [Chemical Engineering], Volume 7, C. Hauser Verlag Munich, 4th Ed. 1986.

Based on these formulations, it is also possible to prepare combinations with other pesticidally active substances, fertilizers andlor growth regulators, for example in the form of a ready mix or a tank mix. Wettable powders are preparations which are uniformly dispersible in water and which, beside the active substance, also comprise wetting agents, for example polyoxyethylated alkylphenols, polyoxyethylated fatty alcohols, alkyl- or alkylphenylsulfonates and dispersants, e.g. sodium lignosulfonate and sodium 2,2'-dinaphthylmethane-6,6'-disulfonate, in addition to a diluent or inert substance.

Emulsifiable concentrates are prepared by dissolving the active substance in an organic solvent, for example butanol, cyclohexanone, dimethylformamide, xylene, or else higher-boiling aromatics or hydrocarbons with addition of one or more emulsifiers. Emulsifiers which can be used are ionic emulsifiers such as, for example, calcium alkylarylsulfonates, such as calcium dodecylbenzenesulfonate, or non-ionic emulsifiers such as, for example, fatty acid polyglycol esters, alkylaryl polyglycol ethers, fatty alcohol polyglycol ethers, propylene oxidel-ethylene oxide condensates, alkyl polyethers, sorbitan fatty acid esters, polyoxyethylene sorbitan fatty acid esters or polyoxyethylene sorbitol esters.

Dusts are obtained by grinding the active substance with finely divided solid substances, for example talc, natural clays such as kaolin, bentonite, pyrophyllite or diatomaceous earth. Granules can be prepared either by spraying the active substance onto adsorptive granulated inert material or by applying active substance concentrates to the surface of carriers such as sand, kaolinites or granulated inert material with the aid of binders, for example polyvinyl alcohol, sodium polyacrylate or else mineral oils. Suitable active substances can also be granulated in the manner customary for the preparation of fertilizer granules, if desired in a mixture with fertilizers.

In wettable powders, the active substance concentration is, for example, approximately 10 to 90% by weight, the remainder to 100% being composed of customary formulation components. In the case of emulsifiable concentrates, the active substance concentration can amount to approximately 5 to 80% by weight. Formulations in the form of dusts usually comprise 5 to 20% by weight of active substance, sprayable solutions approximately 2 to 20% by weight. In the case of granules, the active substance content depends partly on whether the active compound is in liquid or solid form and on which granulation auxiliaries, fillers and the like are being used.

Additionally, the abovementioned formulations of active substances comprise, if appropriate, the tackifiers, wetting agents, dispersants, emulsifiers, penetrants, solvents, fillers or carriers which are customary in each case.

For use, the concentrates which are in commercially available form are, if appropriate, diluted in the customary manner, for example by means of water in the case of wettable powders, emulsifiable concentrates, dispersions and in some cases also microgranules. Preparations in the form of dusts and granules and sprayable solutions are usually not diluted further with other inert substances prior to use.

The rate of application required varies with the external conditions such as, inter alia, temperature and humidity. It can vary within wide limits, for example between 0.0005 and 10.0 kg/ha or more active substance, but it is preferably between 0.001 and 5 kg/ha.

The active substances according to the invention can be present in their commercially available formulations and in the use forms prepared from these formulations in the form of mixtures with other active substances, such as insecticides, attractants, sterilants, acaricides, nematicides, fungicides, ovicides, growth regulators or herbicides.

The pesticides include, for example, phosphoric esters, carbamates, carboxylic esters, formamidines, tin compounds, substances produced by microorganisms and the like.

Preferred components for mixtures are:

1. from the group of the phosphorus compounds acephate, azamethiphos, azinphosethyl, azinphosmethyl, bromophos, bromophosethyl, chlorfenvinphos, chlormephos, chiorpyrifos, chlorpyrifos-methyl, demeton, demeton-S-methyl, demeton-S-methylsulfone, dialifos, diazinon, dichlorvos, dicrotophos, O,O-1,2,2,2-tetrachloroethylphosphorothioate (SD 208 304), dimethoate, disulfoton, EPN, ethion, ethoprophos, etrimfos, famphur, fenamiphos, fenitriothion, fensulfothion, fenthion, fonofos, formothion, heptenophos, isozophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosmet, phosphamidon, phoxim, pirimiphos, pirimiphos-ethyl, pirimiphos-methyl, profenofos, propaphos, proetamphos, prothiofos, pyraclofos, pyridapenthion, quinalphos, suiprofos, temephos, terbufos, tetrachlorvinphos, thiometon, triazophos, trichlorphon, vamidothion;

2. from the group of the carbamates aldicarb, 2-secbutylphenyl methylcarbamate (BPMC), carbaryl, carbofuran, carbosulfan, cloethocarb, benfuracarb, ethiofencarb, furathiocarb, isoprocarb, methomyl, 5-methyl-m-cumenyl butyryl(methyl)carbamate, oxamyl, pirimicarb, propoxur, thiodicarb, thiofanox, ethyl 4,6,9-triaza-4-benzyl,-6,10-dimethyl-8-oxa-7-oxo5,11-dithia-9-dodecenoate (OK 135), 1-methylthio (ethylideneamino)-N-methyl-N-(morpholinothio) carbamate (UC 51717);

3. from the group of the carboxylic esters allethrin, alphametrin, 5-benzyl-3-furylmethyl (E)-(1R)-cis, 2,2-dimethyl-3-(2-oxothiolan-3-ylidenemethyl) cyclopropanecarboxylate, bioallethrin, bioallethrin ((S) cyclopentyl isomer), bioresmethrin, biphenate, (RS)-1-cyano-1-(6-phenoxy-2-pyridyl)methyl (1RS)-trans-3-(4-tert-butylphenyl)-2,2-dimethylcyclopropanecarboxylate (NCI 85193), cycloprothrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D isomer), permethrin, pheothrin ((R)-isomer), d-pralethrin, pyrethrins (natural products), resmethrin, tefluthrin, tetramethrin, tralomethrin;

4. from the group of the amidines amitraz, chlordimeform;

5. from the group of the tin compounds cyhexatin, fenbutatinoxide;

6. others abamectin, Bacillus thuringiensis, bensultap, binapacryl, bromopropylate, buprofezin, camphechlor, cartap, chlorobenzilate, chlorfluazuron, 2-(4-chlorophenyl)-4,5-diphenylthiophene (UBI-T930), chlorfentezine, 2-naphthylmethyl cyclopropanecarboxylate (Ro12-0470), cyromazin, ethyl N-(3,5-dichloro-4-(1,1,2,3,3,3-hexafluoro-1-propyloxy) phenyl)carbamoyl)-2-chlorobenzocarboximidate, DDT, Dicofol, N-(N-(3,5-dichloro-4-(1,1,2,2-tetrafluoroethoxy)phenylamino)carbonyl)-2,6-difluorobenzamide (XRD 473), diflubenzuron, N-(2,3-dihydro-3-methyl-1,3-thiazol-2-ylidene)-2,4-xylidine, dinobuton, dinocap, endosulfan, ethofenprox, (4-ethoxyphenyl)(dimethyl)(3-(3-phenoxyphenyl)propyl)silane, (4-ethoxyphenyl)(3-(4-fluoro-3-phenoxyphenyl)propyl)dimethylsilane, fenoxycarb, 2-fluoro-5-(4-(4-ethoxyphenyl)-4-methyl-1-pentyl) diphenyl ether (MTI 800), granulosis and nuclear polyhedrosis viruses, fenthiocarb, flubenzimine, flucycloxuron, flufenoxuron, gamma-HCH, hexythiazox, hydramethyinon (AC 217300), ivermectin, 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam, trifumuron, imidacloprid.

The active substance content of the use forms prepared from the commercially available formulations can range from 0.00000001 to 95% by weight of active substance, it is preferably between 0.00001 and 1% by weight.

They are applied in a customary manner adapted to the use forms.

The active substances according to the invention are also suitable for controlling endo- and ectoparasites in the field of veterinary medicine and in the field of animal keeping.

The active substances according to the invention are applied by oral administration, for example in the form of tablets, capsules, drinks, granules, by dermal administration, for example by dipping, spraying, pouring-on and spotting-on and dusting, and also by parenteral administration, for example by means of an injection, e.g. s.c.

Accordingly, the novel compound of the formula I according to the invention can also be employed especially advantageously in livestock keeping (for example cattle, sheep, pigs and poultry such as chickens, geese, and the like). In a preferred embodiment of the invention, the novel compounds are administered orally to the animals, if appropriate in the form of suitable formulations (cf. above) and if appropriate together with the drinking water or feed. Since elimination with the feces is efficient, this enables the prevention of the development of insects in the animal's feces in a simple manner. The dosages and formulations which are suitable in each case depend, in particular, on the species and the developmental stage of the productive livestock and also on the infection pressure and can be readily determined and established by the customary methods. In the case of cattle, the novel compounds can be employed for example at dosages of from 0.01 to 1 mg/kg bodyweight.

The compounds of the formula I according to the invention are also distinguished by an outstanding fungicidal activity. Fungal pathogens which have already penetrated the plant tissue can be controlled successfully in a curative fashion. This is especially important and advantageous in the case of those fungal diseases which can no longer be controlled efficiently with the otherwise customary fungicides once infection has set in. The spectrum of action of the claimed compounds includes a variety of economically important phytopathogenic fungi such as, for example, *Plasmopara viticola, Phytophthora infestans, Erysiphe graminis, Pyricularia oryzae, Pyrenophora teres, Leptosphaerea nodorum* und *Pellicularia sasakii* and *Puccinia recondite*.

The compounds according to the invention are in addition also suitable for use in industrial fields, for example as wood preservatives, as preservatives in paints, in cooling lubricants for metalworking, or as preservatives in drilling and cutting oils.

The active substances according to the invention can be used in their commercially available formulations either alone or in combination with other fungicides known from the literature.

Fungicides known from the literature which can be combined in accordance with the invention with the compounds of the formula I are, for example, the following products:

aldimorph, andoprim, anilazine, BAS 480F, BAS 450F, BAS 490F, benalaxyl, benodanil, benomyl, binapacryl, bitertanol, bromuconazole, buthiobate, captafol, captan, carbendazim, carboxin, CGA 173506, cyprodinil, cyprofuram, dichiofluanid, dichlomezin, diclobutrazol, diethofencarb, difenconazole (CGA 169374), difluconazole, dimethirimol, dimethomorph, diniconazole, dinocap, dithianon, dodemorph, dodine, edifenfos, ethirimol, etridiazole, epoxiconazole, fenbuconazole, fenarimol, fenfuram, fenpiclonil, fenpropidin, fenpropimorph, fentin acetate, fentin hydroxide, ferimzone (TF164), fluazinam, fluobenzimine, fludioxinil, fluquinconazole, fluorimide, flusilazole, flutolanil, flutriafol, folpet, fosetyl-aluminum, fuberidazole, fulsulfamide (MT-F 651), furalaxyl, furconazole, furmecyclox, guazatine, hexaconazole, ICI A5504, imazalil, imibenconazole, iprobenfos, iprodione, isoprothiolane, KNF 317, copper compounds such as copper oxychloride, oxine-copper, copper oxide, mancozeb, maneb, mepanipyrim (KIF 3535), metconazol, mepronil, metalaxyl, methasulfocarb, methfuroxam, MON 24000, myclobutanil, nabam, nitrothalidopropyl, nuarimol, ofurace, oxadixyl, oxycarboxin, penconazole, pencycuron, PP 969, probenazole, propineb, prochloraz, procymidon, propamocarb, propiconazole, prothiocarb, pyracarbolid, pyrazophos, pyrifenox, pyrimethanil, pyroquilon, rabenzazole, RH7592, sulfur, tebuconazole, TF 167, thiabendazole, thicyofen, thiofanate-methyl, thiram, toiclofos-methyl, tolylfluanid, triadimefon, triadimenol, triazoxide, tricyclazole, tridemorph, triflumizole, triforine, trifionazol, validamycin, vinchlozolin, XRD 563, zineb, sodium dodecylsulfonate, sodium dodecyl sulfate, sodium C13/C15-alcohol ether sulfonate, sodium cetostearyl phosphate ester, sodium dioctylsulfosuccinate, sodium isopropylnaphthalenesulfonate, sodium methylenebisnaphthalenesulfonate, cetyltrimethylammonium chloride, salts of long-chain primary, secondary or tertiary amines, alkylpropyleneamines, laurylpyrimidinium bromide, ethoxylated quatemized fatty amides, alkyidimethylbenzylammonium chloride and 1-hydroxyethyl-2-alkyl-imidazoline.

The abovementioned components in combinations are known active substances, many of which are described in Ch.R Worthing, S. B. Walker, The Pesticide Manual, 7th edition (1983), British Crop Protection Council. The active substance content of the use forms prepared from the commercially available formulations can vary within wide ranges, the active substance concentration of the use forms can amount to from 0.0001 to 95% by weight of active substance, it is preferably between 0.0001 and 1% by weight. They are applied in a customary manner adapted to suit the use forms.

The examples which follow are intended to illustrate the invention without imposing any limitation thereto.

A. Formulation Examples a) A dust was obtained by mixing 10 parts by weight of active substance and 90 parts by weight of talc as inert substance and comminuting the mixture in a hammer mill.

b) A wettable powder which was readily dispersible in water was obtained by mixing 25 parts by weight of active substance, 65 parts by weight of kaolin-containing quartz as inert substance, 10 parts by weight of potassium lignosulfonate and 1 part by weight of sodium oleoylmethyltaurinate as wetting agent and dispersant and grinding the mixture in a pinned-disk mill.

c) A dispersion concentrate which is readily dispersible in water was prepared by mixing 40 parts by weight of active substance with 7 parts by weight of sulfosuccinic monoester, 2 parts by weight of a sodium lignosulfosuccinate and 51 parts by weight of water and grinding the mixture in a ball mill to a fineness of below 5 microns.

d) An emulsifiable concentrate was prepared from 15 parts by weight of active substance, 75 parts by weight of cyclohexane as solvent and 10 parts by weight of oxyethylated nonylphenol (10 EO) as emulsifier.

e) Granules were prepared from 2 to 15 parts by weight of active substance and an inert carrier material for granules such as attapulgite, pumice granules andlor quartz sand. Expediently, a suspension of the wettable powder from Example b) with a solids content of 30% was used; this was sprayed onto the surface of attapulgite granules and the latter were dried and mixed intimately. The wettable powder amounted to approximately 5% by weight and the inert carrier material to approximately 95% of the finished granules.

B. Preparation Examples

Example A

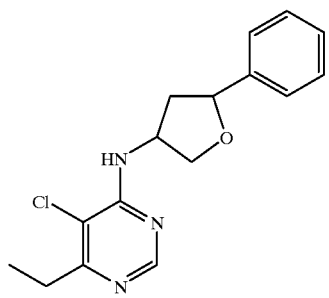

1.) 5-Chloro-6-ethyl-4-(2-phenyltetrahydrofuran-4-ylamino)pyrimidine 1.50 g (8.5 mmol) of 4,5-dichloro-6-ethylpyrimidine, 1.39 g (8.5 mmol) of 4-amino-2-phenyltetrahydrofuran and 2 ml (14 mmol) of triethylamine were heated for 12 hours at 85° C. After cooling, the mixture was diluted with water and extracted with ether, and the organic phase was washed with saturated NaCl solution. After the mixture had been dried and concentrated, the residue was purified by column chromatography using petroleum etherlethyl acetate (9:1, 8:2). This gave 1.63 g (63% of theory) of a colorless oil (diastereomers 1:1).

2.) Preparation of 4-amino-2-phenyltetrahdyrofuran 11.5 g (61 mmol) of 4-azido-2-phenyltetrahydrofuran in 50 ml of THF were added dropwise in the course of 15 minutes at 0° C. to a suspension of 3.46 g (91.1 mmol) of lithium aluminum hydride in 200 ml of THF. The mixture was stirred for 30 minutes at room temperature and refluxed for 1 hour. After the mixture had been cooled to 0° C., excess alanate was destroyed using isopropanol, and the mixture was diluted with 500 ml of ether and washed with saturated tartrate solution and saturated NaCl solution. After the organic phase had been dried and concentrated, the resulting colorless oil was further employed directly. Yield: 9.4 g (95% of theory).

3.) Preparation of 4-azido-2-phenyltetrahydrofuran 14.7 g (61 mmol) of 4-methanesulfonyloxy-2-phenyltetrahydrofuran and 5.13 g (79 mmol) of sodium azide were heated for 3 hours in 120 ml of DMF at 90° C. After the mixture had cooled, it was diluted with ether, washed with water and saturated NaCl solution, dried and concentrated in vacuo. This gave 9.4 g (quant.) of a colorless oil, which was further reacted directly.

4.) Preparation of 4-methanesulfonyloxy-2-phenyltetrahydrofuran 9.2 g (79 mmol) of methanesulfonyl chloride were added dropwise at 0° C. to a solution of 10 g (61 mmol) of 2-phenyltetrahydrofuran-4-ol and 9.2 g (91 mmol) of triethylamine in 150 ml of dichlormethane. The mixture was stirred for 1 hour at 0° C. and then washed with water, 2N hydrochloric acid, saturated $NaHCO_3$ solution and saturated NaCl solution. Drying and concentrating gave 14.7 g (quant.) of mesylate, which was employed further without purification.

5.) Preparation of 2-phenyltetrahydrofuran-4-ol 10 ml of a 60% $HClO_4$ solution was added at 0° C. to a solution of 15 g (91 mmol) of 1-phenyl-3-buten-1-ol epoxide in 400 ml of water/300 ml of acetone. The mixture was stirred for 24 hours at room temperature, 40 ml of concentrated $H_2SO_4$ were added at 0° C., and the mixture was refluxed for 8 hours. After cooling, the mixture was extracted with dichloromethane (3x), washed with saturated $NaHCO_3$, dried and concentrated. Purification by column chromatography using dichlormethanelacetone (9:1, 8:2) gave 10 g (67% of theory) of a colorless oil.

6.) Preparation of 1-phenyl-3-buten-1-ol epoxide 100 ml of hydrogen peroxide (30%) were added dropwise at 0° C. to a solution of 15 g (101 mmol) of 1-phenyl-3-buten-1-ol and 5.5 g (30 mmol) of tetramethylammonium hydroxide in 400 ml of acetonitrile. The mixture was stirred for 4 hours at 0° C. and for 8 hours at room temperature. The mixture was subsequently diluted with ether, the phases were separated, and the organic phase was washed with saturated NaCl solution. Drying and concentrating gave 15 g (90% of theory) of a colorless oil, which was further employed directly.

7.) Preparation of 1-phenyl-3-buten-1-ol 39 g (0.6 mol) of zinc powder were added at 0° C., a little at a time, to a solution of 53 g (0.5 mol) of benzaldehyde and 73 g (0.6 mol) of allyl bromide in 500 ml of saturated NH₄Cl solution/100 ml of THF. The mixture was stirred for 4 hours at room temperature and diluted with ether, and the solid constituents were filtered off with suction. After washing with ether, the phases were separated, and the organic phase was washed with water (2x) and saturated NaCl solution. Drying and concentrating gave 65.2 g (88% of theory) of a colorless oil which was further employed directly.

Example B

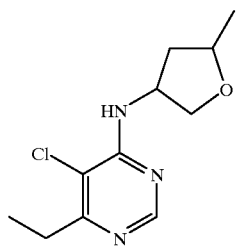

1.) 5-Chloro-6-ethyl-4-(2-methyltetrahydrofuran-4-ylamino)pyrimidine 1.5 g of 4,5-dichloro-6-ethylpyrimidine (8.5 mmol), 0.86 g (8.5 mmol) of 4-amino-2-methyltetrahydrofuran (prepared from 2-methyltetrahydrofuran4-ol analogously to the route given for Example A) and 2 ml (14 mmol) of triethylamine were heated for 6 hours at 85° C. After cooling, the mixture was diluted with water and extracted with ether, and the organic phase was washed with saturated NaCl solution. After drying and concentrating, the residue was purified by column chromatography using petroleum ether/ethyl acetate (8:2, 7:3). This gave 1.73 g (84% of theory) of a colorless oil (diastereomers 2:1).

2.) Preparation of the starting material 2-methyltetrahydrofuran-4-ol 4.6 g (0.121 mol) of sodium borohydride were added in portions at 0° C. to a solution of 12.1 g (0.121 mol) of 2-methyltetrahydrofuran-4-one (M. A. Guantunco, P. Friedel and A. S. Giammarino, Tetrahedron (1964,20, 1763) in 150 ml of methanol. The mixture was stirred for 1 hour at 0° C., 150 ml of 5% sodium hydroxide solution were added, and the mixture was extracted with ethyl acetate. The combined organic phases were washed with water and saturated NaCl solution, dried and concentrated. This gave 8.3 g (67% of theory) of a colorless oil which was further employed directly.

Example C

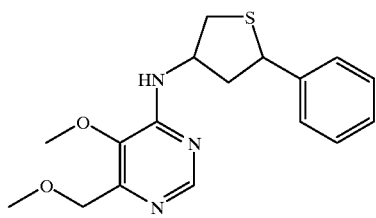

1.) 5-Methoxy-6-methoxymethyl-4-(2-phenyltetrahydrothiophen-4-ylamino)pyrimidine 1.6 g (8.5 mmol) of 4-chloro-5-methoxy-6-methoxymethylpyrimidine, 1.5 g (8.5 mmol) of 4-amino-2-phenyltetrahydrothiophene (prepared from 2-phenyl-4-oxo-tetrahydrothiophene (cf. D. N. Reinhard, W. P. Trompenaars, I. Geevers, Synthesis 1978, 368) analogously to the route given in Example B) and 2 ml (14 mmol) of triethylamine were heated for 24 hours at 85° C. After cooling, the mixture was diluted with water and extracted with ether, and the organic phase was washed with saturated NaCl solution. After drying and concentrating, the residue was purified by column chromatography using petroleum ether/ethyl acetate (9:1). This gave 1.18 g (42% of theory) of a pale yellow syrup.

Example D

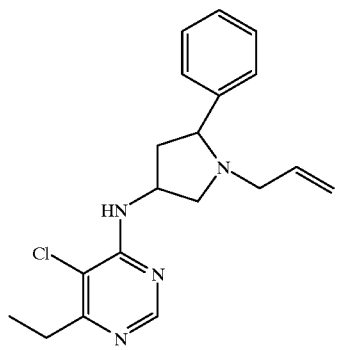

1.) 5-Chloro-6-ethyl-(1-allyl-2-phenylpyrrolidin-4-ylamino)pyrimidine 1.5 g (8.5 mmol) of 4,5-dichloro-6-ethylpyrimidine, 1.7 g (8.5 mmol) of 1-allyl-4-amino-2-phenylpyrrolidine (prepared from 1-allyl-2-phenylpyrrolidin--4-ol analogously to the route described in Example A) and 2 ml (4 mmol) of triethylamine were heated for 12 hours at 85° C. After cooling, the mixture was diluted with water and extracted with ether, and the organic phase was washed with saturated NaCl solution. After drying and concentrating, the residue was purified by column chromatography using petroleum ether/ethyl acetate (9:1, 8:2). This gave 0.95 g (33% of theory) of a colorless syrup (diastereomers 1:1)

2.) Preparation of the starting material 1-allyl-2-phenylpyrrolidin-4-ol 14.7 g (128 mmol) of methanesulfonyl chloride were added dropwise at 0° C. to a solution of 16.2 g (98.2 mmol) of 1-phenyl-3-buten-1-ol epoxide and 15 g (148 mmol) of triethylamine in 130 ml of dichloromethane. The mixture was stirred for 1 hour at 0° C., 60 ml (790 mmol) of allylamine were added, and the mixture was stirred for 10 hours at room temperature. The mixture was subsequently washed with saturated NaHCO₃ solution, dried and concentrated, and the residue was purified by column chromatography using petroleum ether/ethyl acetate (7:3; 1% diisopropylamine). This gave 8.2 g (41% of theory) of a colorless oil.

Example E

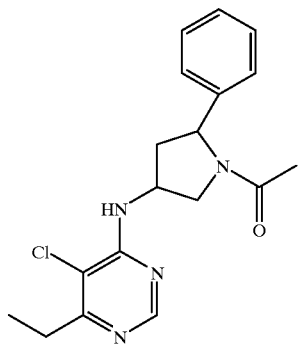

1.) 5-Chloro-6-ethyl-4-(1-acetyl-2-phenylpyrrolidin4-ylamino)pyrimidine

A 4-necked flask equipped with dropping funnel and distillation bridge was charged with 3.1 g (9 mmol) of 5-chloro-6-ethyl-4-(1-allyl-2-phenylpyrrolidon-4-ylamino)pyrimidine, 300 mg of tris(triphenylphosphine)rhodium(I) chloride, 140 ml of acetonitrile and 30 ml of water under a stream of $N_2$. The mixture was heated in such a way that the solvent mixture distilled off while simultaneously the same volume of the mixture was returned via the dropping funnel. After 7 hours, the mixture was cooled and diluted with dichloromethane, the phases were separated, and the organic phase was washed with saturated NaCl solution. After the mixture had been dried and evaporated on a rotary evaporator, the residue was dissolved in 30 ml of dichloromethane and treated with 1.4 g (14 mmol) of triethylamine and 1.2 g (12 mmol) of acetic anhydride. After the solution had been stirred for 30 minutes, it was treated with water and washed with saturated $NaHCO_3$ and saturated NaCl solution. The organic phase was dried and concentrated and the residue was purified by column chromatography using petroleum ether/ethyl acetate (7:3, 1:1, 1% diisopropylamine). This gave 1.2 g (40% of theory) as a pale yellow oil (diastereomers 1:1).

Example F

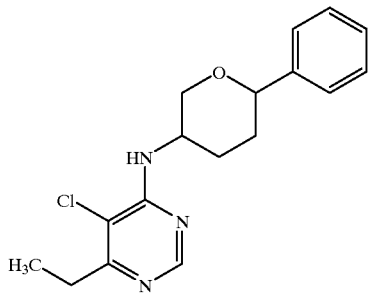

1.) 5-Chloro-6-ethyl-4-(2-phenyltetrahydropyran-5-ylamino)pyrimidine 2.4 g (13.5 mmol) of 4,5-dichloro-6-ethylpyrimidine, 2.4 g (13.5 mmol) of 5-amino-2-phenyltetrahydropyran (prepared from 2-phenyltetrahydropyran-5-ol (cf. U.S. Pat. No. 4,388,104) analogously to the routes described in Example A) and 3 ml (21 mmol) of triethylamine were heated for 12 hours at 85° C. After cooling, the mixture was diluted with water and extracted with ether, and the organic phase was washed with saturated NaCl solution. After drying and concentrating, the residue was purified by column chromatography using petroleum ether/ethyl acetate (9:1, 8:2). This gave 0.65 g (15% of theory) of the trans isomer as a colorless oil and 2.17 g (51% of theory) of the cis isomer as a colorless oil.

The compounds of the tables which follow are obtained analogously to Examples A to F.

TABLE 1

| Ex. No. | $R^2$ | $R^3$ | $R^4$ | $R^6$ | X | Z | M.p. [° C.] |
|---|---|---|---|---|---|---|---|
| 1 | $C_2H_5$ | Cl | H | H | NH | O | 67 |
| 2 | $CH_3OCH_2$ | $OCH_3$ | H | H | NH | O | |
| 3 | $C_2H_5$ | Cl | H | $CH_3$ | NH | O | Oil |
| 4 | $C_2H_5$ | Br | H | $CH_3$ | NH | O | Oil |
| 5 | $CH_3OCH_2$ | $OCH_3$ | H | $CH_3$ | NH | O | Oil |
| 6 | $C_2H_5$ | Cl | H | $CH_3$ | O | O | |
| 7 | $(CH)_4$ | | H | $CH_3$ | NH | O | 135 |
| 8 | $C_2H_5$ | Cl | H | $CF_3$ | NH | O | 54 |
| 9 | $CH_3OCH_2$ | $OCH_3$ | H | $CF_3$ | NH | O | Oil |
| 10 | $C_2H_5$ | Cl | H | $CF_3$ | O | O | Oil |
| 11 | $(CH)_4$ | | H | $CF_3$ | O | O | 75 |
| 12 | $C_2H_5$ | Cl | $CH_3$ | $CH_3$ | NH | O | Oil |
| 13 | $CH_3OCH_2$ | $OCH_3$ | $CH_3$ | $CH_3$ | Nh | O | Oil |
| 14 | $C_2H_5$ | Cl | $CH_3$ | $CH_3$ | O | O | Oil |
| 15 | $(CH)_4$ | | $CH_3$ | $CH_3$ | O | O | Oil |
| 16 | $C_2H_5$ | Cl | H | $C_2H_5$ | NH | O | Oil |
| 17 | $C_2H_5$ | Br | H | $C_2H_5$ | NH | O | |
| 18 | $CH_3OCH_2$ | $OCH_3$ | H | $C_2H_5$ | NH | O | Oil |
| 19 | $C_2H_5$ | Cl | H | $C_2H_5$ | O | O | |
| 20 | $(CH)_4$ | | H | $C_2H_5$ | O | O | |
| 21 | $C_2H_5$ | Cl | H | $n-C_3H_7$ | NH | O | Oil |
| 22 | $C_2H_5$ | Br | H | $n-C_3H_7$ | NH | O | Oil |
| 23 | $CH_3OCH_2$ | $OCH_3$ | H | $n-C_3H_7$ | NH | O | Oil |
| 24 | $C_2H_5$ | Cl | H | $n-C_3H_7$ | O | O | Oil |
| 25 | $(CH)_4$ | | H | $n-C_3H_7$ | NH | O | 153 |
| 26 | $C_2H_5$ | Cl | H | $i-C_3H_7$ | NH | O | Oil |
| 27 | $C_2H_5$ | Br | H | $i-C_3H_7$ | NH | O | |
| 28 | $CH_3OCH_2$ | $OCH_3$ | H | $i-C_3H_7$ | NH | O | Oil |
| 29 | $C_2H_5$ | Cl | H | $n-C_4H_9$ | NH | O | Oil |
| 30 | $C_2H_5$ | Br | H | $n-C_4H_9$ | NH | O | |
| 31 | $CH_3OCH_2$ | $OCH_3$ | H | $n-C_4H_9$ | NH | O | Oil |
| 32 | $C_2H_5$ | Cl | H | $n-C_4H_9$ | O | O | |
| 33 | $(CH)_4$ | | H | $n-C_4H_9$ | O | O | Oil |
| 34 | $C_2H_5$ | Cl | H | $t-C_4H_9$ | NH | O | Oil |
| 35 | $C_2H_5$ | Br | H | $t-C_4H_9$ | NH | O | Oil |
| 36 | $CH_3OCH_2$ | $OCH_3$ | H | $t-C_4H_9$ | NH | O | |
| 37 | $C_2H_5$ | Cl | H | $n-C_5H_{11}$ | NH | O | Oil |
| 38 | $C_2H_5$ | Br | H | $n-C_5H_{11}$ | NH | O | |
| 39 | $CH_3OCH_2$ | $OCH_3$ | H | $n-C_5H_{11}$ | NH | O | |
| 40 | $C_2H_5$ | Cl | H | $n-C_5H_{11}$ | O | O | Oil |
| 41 | $(CH)_4$ | | H | $n-C_5H_{11}$ | O | O | Oil |
| 42 | $C_2H_5$ | Cl | H | $CH_2OCH_3$ | O | O | |
| 43 | $(CH)_4$ | | H | $CH_2OCH_3$ | O | O | |
| 44 | $C_2H_5$ | Cl | H | $CH_2OCH_3$ | NH | O | Oil |
| 45 | $C_2H_5$ | Br | H | $CH_2OCH_3$ | NH | O | Oil |
| 46 | $CH_3OCH_2$ | $OCH_3$ | H | $CH_2OCH_3$ | NH | O | Oil |
| 47 | $(CH)_4$ | | H | $CH_2OCH_3$ | NH | O | |
| 48 | $C_2H_5$ | Cl | H | phenyl | NH | O | Oil |
| 49 | $CH_3OCH_2$ | $OCH_3$ | H | phenyl | NH | O | Oil |
| 50 | $(CH)_4$ | | H | phenyl | NH | O | Oil |
| 51 | $C_2H_5$ | Cl | H | phenyl | O | O | Oil |

TABLE 1-continued

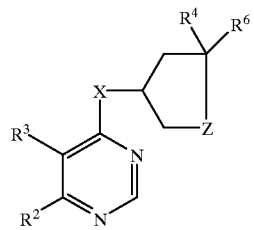

| Ex. No. | R² | R³ | R⁴ | R⁶ | X | Z | M.p. [° C.] |
|---|---|---|---|---|---|---|---|
| 52 | (CH)₄ | | H | phenyl | O | O | Oil |
| 53 | C₂H₅ | Cl | CH₃ | phenyl | NH | O | Oil |
| 54 | C₂H₅ | Cl | CH₃ | phenyl | O | O | Oil |
| 55 | (CH)₄ | | CH₃ | phenyl | O | O | 85 |
| 56 | C₂H₅ | Cl | H | 2-methyl-phenyl | NH | O | |
| 57 | CH₃OCH₂ | OCH₃ | H | 2-methyl-phenyl | NH | O | |
| 58 | C₂H₅ | Cl | H | 3-methyl-phenyl | NH | O | |
| 59 | CH₃OCH₂ | OCH₃ | H | 3-methyl-phenyl | NH | O | |
| 60 | C₂H₅ | Cl | H | 4-methyl-phenyl | NH | O | 96 |
| 61 | CH₃OCH₂ | OCH₃ | H | 4-methyl-phenyl | NH | O | Oil |
| 62 | C₂H₅ | Cl | H | 4-methyl-phenyl | O | O | Oil |
| 63 | (CH)₄ | | H | 4-methyl-phenyl | O | O | Oil |
| 64 | C₂H₅ | Cl | H | 3,5-di-methyl-phenyl | NH | O | |
| 65 | C₂H₅ | Cl | H | 3,4-di-methyl-phenyl | NH | O | |
| 66 | C₂H₅ | Cl | H | 4-methoxyphenyl | NH | O | Oil |
| 67 | CH₃OCH₂ | OCH₃ | H | 4-methoxyphenyl | NH | O | Oil |
| 68 | C₂H₅ | Cl | H | 3-fluoro-phenyl | NH | O | Oil |
| 69 | CH₃OCH₂ | OCH₃ | H | 3-fluoro-phenyl | NH | O | |
| 70 | C₂H₅ | Cl | H | 4-fluoro-phenyl | NH | O | 73 |
| 71 | CH₃OCH₂ | OCH₃ | H | 4-fluoro-phenyl | O | O | Oil |
| 72 | C₂H₅ | Cl | H | 4-fluoro-phenyl | O | O | Oil |
| 73 | (CH)₄ | | H | 4-fluoro-phenyl | O | O | 77 |
| 74 | C₂H₅ | Cl | H | 3-chloro-phenyl | NH | O | |
| 75 | CH₃OCH₂ | OCH₃ | H | 3-chloro-phenyl | NH | O | |
| 76 | C₂H₅ | Cl | H | 4-chloro-phenyl | NH | O | |
| 77 | CH₃OCH₂ | OCH₃ | H | 4-chloro-phenyl | NH | O | |
| 78 | C₂H₅ | Cl | H | 3-bromo-phenyl | NH | O | |
| 79 | CH₃OCH₂ | OCH₃ | H | 3-bromo-phenyl | NH | O | |
| 80 | C₂H₅ | Cl | H | 4-bromo-phenyl | NH | O | Oil |
| 81 | CH₃OCH₂ | OCH₃ | H | 4-bromo-phenyl | NH | O | |
| 82 | C₂H₅ | Cl | H | 4-iodo-phenyl | NH | O | |
| 83 | CH₃OCH₂ | OCH₃ | H | 4-iodo-phenyl | NH | O | |
| 84 | C₂H₅ | Cl | H | 3-trifluoro-methoxy | NH | O | Oil |
| 85 | CH₃OCH₂ | OCH₃ | H | 3-trifluoro-methoxy | NH | O | |
| 86 | C₂H₅ | Cl | H | 4-trifluoro-methoxy | NH | O | Oil |
| 87 | CH₃OCH₂ | OCH₃ | H | 4-trifluoro-methoxy | NH | O | |
| 88 | C₂H₅ | Cl | H | 4-phenyl-phenyl | NH | O | Oil |
| 89 | C₂H₅ | Cl | H | 4-phenoxy-phenyl | NH | O | Oil |
| 90 | C₂H₅ | Cl | H | 4-phenoxyphenyl | O | O | Oil |
| 91 | (CH)₄ | | H | 4-phenoxyphenyl | O | O | Oil |
| 92 | C₂H₅ | Cl | H | 4-nitro-phenyl | NH | O | 102 |
| 93 | CH₃OCH₂ | OCH₃ | H | 4-nitro-phenyl | NH | O | |
| 94 | C₂H₅ | Cl | H | furan-2-yl | NH | O | Oil |
| 95 | C₂H₅ | Cl | H | phenyl | NH | S | 110–112 |
| 96 | CH₃OCH₂ | OCH₃ | H | phenyl | NH | S | Oil |
| 97 | C₂H₅ | Cl | H | 4-chloro-phenyl | NH | S | Oil |
| 98 | C₂H₅ | Cl | H | 4-chloro-phenyl | NH | SO | 85–86 |
| 99 | C₂H₅ | Cl | H | 4-chloro-phenyl | NH | SO₂ | 132–133 |
| 100 | CH₃OCH₂ | OCH₃ | H | 4-chloro-phenyl | NH | S | Oil |
| 101 | C₂H₅ | Cl | H | 4-methoxyphenyl | NH | SO | 121–122 |
| 102 | C₂H₅ | Cl | H | 4-methoxyphenyl | NH | SO | 92–93 |
| 103 | C₂H₅ | Cl | H | 4-methoxyphenyl | NH | SO₂ | 167–169 |
| 104 | CH₃OCH₂ | OCH₃ | H | 4-methoxyphenyl | NH | S | Oil |

TABLE 2

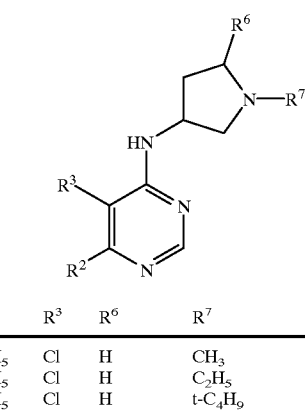

| Ex. No. | R² | R³ | R⁶ | R⁷ | M.p. [° C.] |
|---|---|---|---|---|---|
| 105 | C₂H₅ | Cl | H | CH₃ | |
| 106 | C₂H₅ | Cl | H | C₂H₅ | |
| 107 | C₂H₅ | Cl | H | t-C₄H₉ | |

TABLE 2-continued

| Ex. No. | $R^2$ | $R^3$ | $R^6$ | $R^7$ | M.p. [°C.] |
|---|---|---|---|---|---|
| 108 | $C_2H_5$ | Cl | phenyl | H | oil |
| 109 | $C_2H_5$ | Cl | phenyl | $CH_3$ | |
| 110 | $C_2H_5$ | Cl | phenyl | $C_2H_5$ | |
| 111 | $C_2H_5$ | Cl | phenyl | allyl | oil |
| 112 | $C_2H_5$ | Cl | phenyl | $i\text{-}C_3H_7$ | oil |
| 113 | $C_2H_5$ | Cl | phenyl | $t\text{-}C_4H_9$ | oil |
| 114 | $C_2H_5$ | Cl | phenyl | phenyl | 43 |
| 115 | $C_2H_5$ | Cl | phenyl | benzyl | oil |
| 116 | $C_2H_5$ | Cl | phenyl | formyl | 113 |
| 117 | $C_2H_5$ | Cl | phenyl | acetyl | 120 |
| 118 | $C_2H_5$ | Cl | phenyl | benzoyl | |
| 119 | $C_2H_5$ | Cl | phenyl | $CH_3SO_2$ | 140 |
| 120 | $C_2H_5$ | Cl | phenyl | $CF_3SO_2$ | |
| 121 | $C_2H_5$ | Cl | phenyl | $CH_2SCH_3$ | |
| 122 | $C_2H_5$ | Cl | phenyl | $CH_2OCH_3$ | |
| 123 | $C_2H_5$ | Cl | phenyl | $CON(CH_3)_2$ | oil |
| 124 | $C_2H_5$ | Cl | phenyl | CON(H)phenyl | 57 |
| 125 | $C_2H_5$ | Cl | phenyl | $COOCH_3$ | |

TABLE 3

| Ex. Nr. | $R^2$ | $R^3$ | $R^4$ | $R^6$ | Isomer | Z | M.p. [°C.] |
|---|---|---|---|---|---|---|---|
| 126 | $C_2H_5$ | Cl | H | H | | O | oil |
| 127 | $CH_3OCH_2$ | $OCH_3$ | H | H | | O | |
| 128 | $C_2H_5$ | Cl | H | $CH_3$ | trans | O | |
| 129 | $C_2H_5$ | Cl | H | $CH_3$ | cis | O | |
| 130 | $CH_3OCH_2$ | $OCH_3$ | H | $CH_3$ | trans | O | |
| 131 | $CH_3OCH_2$ | $OCH_3$ | H | $CH_3$ | cis | O | |
| 132 | $C_2H_5$ | Cl | H | $t\text{-}C_4H_9$ | trans | O | |
| 133 | $C_2H_5$ | Cl | H | $t\text{-}C_4H_9$ | cis | O | |
| 134 | $CH_3OCH_2$ | $OCH_3$ | H | $t\text{-}C_4H_9$ | trans | O | |
| 135 | $CH_3OCH_2$ | $OCH_3$ | H | $t\text{-}C_4H_9$ | cis | O | |
| 136 | $C_2H_5$ | Cl | H | phenyl | trans | O | oil |
| 137 | $C_2H_5$ | Cl | H | phenyl | cis | O | oil |
| 138 | $CH_3OCH_2$ | $OCH_3$ | H | phenyl | trans | O | |
| 139 | $CH_3OCH_2$ | $OCH_3$ | H | phenyl | cis | O | |
| 140 | $C_2H_5$ | Cl | $CH_3$ | phenyl | trans | O | |
| 141 | $C_2H_5$ | Cl | $CH_3$ | phenyl | cis | O | |
| 142 | $C_2H_5$ | Cl | H | 3-methylphenyl | trans | O | |
| 143 | $C_2H_5$ | Cl | H | 3-methylphenyl | cis | O | |
| 144 | $C_2H_5$ | Cl | H | 4-methylphenyl | trans | O | 99 |
| 145 | $C_2H_5$ | Cl | H | 4-methylphenyl | cis | O | 71 |
| 146 | $C_2H_5$ | Cl | H | 4-methoxyphenyl | trans | O | |
| 147 | $C_2H_5$ | Cl | H | 4-methoxyphenyl | cis | O | |
| 148 | $C_2H_5$ | Cl | H | 4-fluorophenyl | trans | O | |
| 149 | $C_2H_5$ | Cl | H | 4-fluorophenyl | cis | O | |
| 150 | $C_2H_5$ | Cl | H | 4-chlorophenyl | trans | O | |
| 151 | $C_2H_5$ | Cl | H | 4-chlorophenyl | cis | O | |
| 152 | $C_2H_5$ | Cl | H | 4-bromophenyl | trans | O | |

TABLE 3-continued

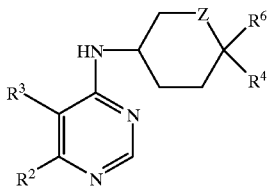

| Ex. Nr. | $R^2$ | $R^3$ | $R^4$ | $R^6$ | Isomer | Z | M.p. [° C.] |
|---|---|---|---|---|---|---|---|
| 153 | $C_2H_5$ | Cl | H | 4-bromophenyl | cis | O | |
| 154 | $C_2H_5$ | Cl | H | 4-trifluoromethyl | trans | O | |
| 155 | $C_2H_5$ | Cl | H | 4-trifluoromethyl | cis | O | |
| 156 | $C_2H_5$ | Cl | H | 4-difluoro-methoxyphenyl | trans | O | |
| 157 | $C_2H_5$ | Cl | H | 4-difluoro-methoxyphenyl | cis | O | |
| 158 | $C_2H_5$ | Cl | H | 4-trifluoro-methoxyphenyl | trans | O | |
| 159 | $C_2H_5$ | Cl | H | 4-trifluoro-methoxyphenyl | cis | O | |
| 160 | $C_2H_5$ | Cl | H | 4-trifluoromethyl | trans | O | |
| 161 | $C_2H_5$ | Cl | H | 4-trifluoromethyl | cis | O | |
| 162 | $C_2H_5$ | Cl | H | 4-n-butylphenyl | trans | O | |
| 163 | $C_2H_5$ | Cl | H | 4-n-butylphenyl | cis | O | |
| 164 | $C_2H_5$ | Cl | H | 4-t-butylphenyl | trans | O | |
| 165 | $C_2H_5$ | Cl | H | 4-t-butylphenyl | cis | O | |
| 166 | $C_2H_5$ | Cl | H | dioxolan-2-yl | trans | O | |
| 167 | $C_2H_5$ | Cl | H | dioxolan-2-yl | cis | O | |
| 168 | $C_2H_5$ | Cl | H | 1,3-dioxan-2-yl | trans | O | |
| 169 | $C_2H_5$ | Cl | H | 1,3-dioxan-2-yl | cis | O | |
| 170 | $C_2H_5$ | Cl | H | methoxymethyl | trans | O | |
| 171 | $C_2H_5$ | Cl | H | methoxymethyl | cis | O | |
| 172 | $C_2H_5$ | Cl | H | hydroxyethyl | trans | O | |
| 173 | $C_2H_5$ | Cl | H | hydroxyethyl | cis | O | |
| 174 | $C_2H_5$ | Cl | H | 2-hydroxy-2-propyl | trans | O | |
| 175 | $C_2H_5$ | Cl | H | 2-hydroxy-2-propyl | cis | O | |
| 176 | $C_2H_5$ | Cl | H | ethenyl | trans | O | |
| 177 | $C_2H_5$ | Cl | H | ethenyl | cis | O | |
| 178 | $C_2H_5$ | Cl | H | propan-2-yl | trans | O | |
| 179 | $C_2H_5$ | Cl | H | propan-2-yl | cis | O | |
| 180 | $C_2H_5$ | Cl | H | ethoxy | trans | O | |
| 181 | $C_2H_5$ | Cl | H | ethoxy | cis | O | |
| 182 | $C_2H_5$ | Cl | H | 2-methyl-1-propoxy | trans | O | |
| 183 | $C_2H_5$ | Cl | H | 2-methyl-1-propoxy | cis | O | |

C. Biological Examples

Use as Fungicide

The activity of the preparations according to the invention was assessed using a 0–4 scale, in which 0 means a disease suppression of 0–24%
1 means a disease suppression of 25–49%
2 means a disease suppression of 50–74%
3 means a disease suppression of 75–97%
4 means a disease suppression of 97–100%.

Example G

Barley plants cv. "Maris Otter" in the 2-leaf stage were sprayed to run-off with a solution of the compound according to the invention in a mixture of 40% of acetone and 60% of water. 24 hours later, the plants were inoculated with conidia of powdery mildew of barley (*Erysiphe graminis* f. sp. *hordei*) and kept in a controlled-environment cabinet at 20° C. and a relative atmospheric humidity of 75–80%. 7 days after the treatment, the plants were examined for symptoms of powdery mildew of barley. The following compounds scored 3 at 500 mg of active substance/I spray mixture:

Compounds of Examples No. 5, 7, 36.

Example H

Tomato plants cv. "First in the Field" in the 3–4-leaf stage were sprayed to run-off with a solution of the compound according to the invention in a mixture of 40% of acetone and 60% of water. 24 hours later, the plants were inoculated with a spore suspension of *Phytophthora infestans* (20,000 spores/ml) and kept in a controlled-environment cabinet at 15° C., first for 2 days at a relative atmospheric humidity of 99% and then for 4 days at a relative atmospheric humidity of 75–80%. 6 days after the treatment, the plants were examined for symptoms of *Phytophthora infestans*. The following compounds scored 3 or 4 at 500 mg of active substance/I spray mixture:

Compounds of Examples No. 5, 96, 103.

Example I

Grapevine seedings cv. "Grüner Veltliner" approximately 6 weeks old were sprayed to runoff with a solution of the compound according to the invention in a mixture of 40% of acetone and 60% of water. 24 hours later, the plants were inoculated by spraying with a Zoospore suspension (100,000/ml) of *Plasmopora viticola* and kept in a controlled-environment cabinet at 70° C. and a relative atmospheric humidity of approximately 99%. 14 days after the treatment, the plants were examined for symptoms of *Plasmopora viticola*. The following compounds scored 3 or 4 at 500 mg of active substances spray mixture:

Compounds of Examples No. 9, 10, 11, 13, 16, 22, 23, 25, 29, 31, 32, 33, 34, 50, 53, 61, 67, 68, 70, 71, 80, 84, 86, 89, 113.

Example K

Wheat plants cv. "Hornet" in the 2-leaf stage were sprayed to run-off with a solution of the compound according to the invention in a mixture of 40% of acetone and 60% of water. 24 hours later, the plants were inoculated by spraying with a pyknospore suspension (500,000/ml) of Leptosphaeria nodorum and kept in a controlled-environment cabinet at 18–20° C. and a relative atmospheric humidity of approximately 99%. 14 days after innoculation, the plants were examined for symptoms of *Leptosphaeria nodorum*.

The following compounds scored 3 or 4 at 500 mg of active substance/I spray mixture:

Compounds of Examples No.18, 22, 23, 25, 28, 34, 36, 50, 53, 55, 63, 70, 71, 73, 80, 86, 119.

Example L

Rice plants cv. "Nihonbare" in the 1.5-leaf stage were sprayed to run-off with a solution of the compound according to the invention in a mixture of 40% of acetone and 60% of water. A solution of the substance in a mixture of 5% of acetone and 95% of water was applied simultaneously by pouring. 24 hours later, the plants were inoculated by spraying with a pyknospore suspension ($10^6$/ml) of *Pyricularia oryzae*. The plants were kept for 2 days in a darkened controlled-environment cabinet at 26° C. and a relative atmospheric humidity of 99% and subsequently transferred into an illuminated controlled-environment cabinet at approximately 18° C. and a relative atmospheric humidity of 75–80%. 7–9 days afger innoculation, the plants were examined for symptoms of *Pyricularia oryzae*.

The following substances scored 3 or 4 at 500 mg of active substance/I spray mixture:

Compounds of Examples No. 1, 9, 21, 22, 23, 25, 26, 31, 34, 36, 37, 38, 48, 49, 53, 70, 86, 90, 91, 111.

Example M

Apple seedlings (Malus sp.) approximately 3 weeks old were sprayed to runoff with a solution of the compound according to the invention in a mixture of 40% of acetone and 60% of water. After 24 hours, the plants were inoculated by spraying with a spore suspension (300,000/mi) of *Venturia inaequalis*. The plants were kept for 2 days in the dark at 18–20° C. and a relative atmospheric humidity of 99%, subsequently in the light for 5 days at the same atmospheric humidity and finally for 7 days at an atmospheric humidity of 75–80%. 14 days after the treatment, the plants were examined for symptoms of *Venturia inaequalis*.

The following substances scored 3 or 4 at 500 mg of active substance/I of spray mixture:

Compounds according to Examples No. 21, 23, 36.

Example N

Tomato plants cv. "First in the Field" in the 2–3-leaf stage were sprayed to run-off with a solution of the compound according to the invention in a mixture of 40% of acetone and 60% of water. After 24 hours, the plants were inoculated with a spore suspension (500,000/ml) of *Botrytis cinerea*. The plants were kept in a conrolled-environment cabinet at 18–20° C. and a relative atmospheric humidity of 99%. 5 days after innoculation, the plants were examined for symptoms of *Botrytis cinerea*. The following substances scored 3 or 4 at 500 mg of active substance/I spray mixture:

Compounds of Examples No. 23, 71, 84, 99.

Use as Insecticide/acaricide

Example O

Portions of 1 ml of the test formulation, emulsified in water, were applied uniformly to the insides of the dish and of the cover of a Petri dish and, after the coating had dried on, batches of 10 imagines of the common housefly (*Musca domestica*) were introduced. After the dishes had been closed, they were kept at room temperature, and the mortality of the test animals was determined after 3 hours. At 300 ppm (active substance content in the test solution), the preparations of Examples No.3, 4, 21, 22, 23, 34, 35, 36, 48, 49, 60, 61, 68, 71, 80, 86, 137 showed 100% mortality of the test animals which had been introduced.

Example P

Rice seed was germinated on cotton wool in glass culture dishes under moist conditions and after they had grown to a stem length of approximately 8 cm, the leaves were introduced into the test solution. After the solution had run off, the treated rice plants were introduced into culture containers separately for each test concentration and populated with batches of 10 larvae (L3) of the species *Nilaparvata lugens*. After the sealed culture containers had been kept at 21° C., the mortality of the leafhopper larvae was determind after 4 days. At a concentration of 300 ppm (active substance content in the test solution), 100% mortality of the test animals introduced was shown by the preparations of Examples No. 8, 9, 21, 22, 23, 38, 48, 49, 50, 60, 71, 80, 84, 86, 42, 137.

Example Q

Wheat seed was pregerminated for 6 hours under water and then transferred into 10 ml glass test tubes and covered with 2 ml of soil in each case. After 1 ml of water had been added, the plants remained in the culture tubes at room temperature (21° C.) until they had reached a plant height of approximately 3 cm. *Diabrotical undecimpunctata* larvae in the middle stage (batches of 10) were subsequently introduced onto the soil in the glass tubes and, after 2 hours, 1 ml of the test liquid in the concentration to be tested was pipefted onto the soil surface in the glass tubes. After they had been left to stand for 5 days under laboratory conditions (21° C.), soil and roots were examined for live Diabrotica larvae and the mortality was determined. At 300 ppm (active substance content in the test solution), 100% mortality of the test animals which had been introduced was shown by the preparations of Examples No.3, 4, 8, 9, 11, 16, 18, 21, 22, 23, 26, 29, 33, 34, 35, 36, 37, 38, 39, 41, 48, 49, 50, 53, 68, 70, 80, 84, 86, 94, 96, 97, 98, 100, 104, 111, 137.

Example R

Field beans (*Vicia faba*) which were severely populated with the black bean aphid (*Aphis fabae*) were sprayed with aqueous dilutions of wettable powder concentrates with an active substance content of 300 ppm to the stage of beginning run-off. The mortality of the aphids was determined after 3 days. A 100% destruction was achieved with the compounds of Examples No. 21, 22, 23, 26, 27, 29, 37, 38, 60, 61, 67, 68, 70, 71, 80, 84, 86, 137.

Example S

Bean plants (Phaseolus v.) which were severely infested with greenhouse red spider mites (*Tetranychus urticae*, full population) were sprayed with the aqueous dilution of a wettable powder concentrate which contained 300 ppm of the active substance in question. The mortality of the mites was checked after 7 days. 100% destruction was achieved with the compounds of Examples No. 9, 48, 49, 61, 66, 67, 68, 70, 71, 80, 86, 89, 137.

Use as Ovicide

Example T

Filter paper disks supporting eggs of the large milkweed bug (*Oncopeltus fasciatus*) were each treated with 0.5 ml portions of aqueous dilution of the test formulation. After the coating had dried on, the Petri dish was closed and the inside was kept at maximum atmospheric humidity. After the dishes had been kept at room temperature, the ovicidal activity was determined after 7 days. At an active substance content of 300 ppm, 100% ovicidal activity was achieved by the compounds of Examples No. 3, 4, 21, 22, 23, 34, 36, 48, 49, 90, 60, 61, 68, 70, 71, 80, 86, 92, 100, 137.

Use as antiparasitic

Example U

In-vitro test on tropical cattle ticks (*Boophilus microplus*)

The activity of the compounds according to the invention against ticks was demonstrated in the following experimental set-up:

To produce a suitable preparation of active substance, the active substances were dissolved at a concentration of 10% (w/v) in a mixture composed of dimethylformamide (85 g), nonylphenyl polyglycol ether (3 g) and oxyethylated castor oil (7 g) and the resulting emulsion concentrates were diluted with water to a test concentration of 500 ppm.

Batches of ten female tropical ticks, *Boophilus microplus,* which had sucked themselves full were immersed for five minutes in these dilutions of active substance. The ticks were subsequently dried on filter paper and then attached, with 25 their backs, to an adhesive film in order to deposit eggs. The ticks were kept in an incubator at 28° C. and an atmospheric humidity of 90%. For the control, female ticks were immersed in water only. The activity was assessed on the basis of the inhibition of egg deposition two weeks after the treatment.

In this test, the compounds of examples no. 21, 34, 37, 38, 39, 70, 86 caused in each case 100% inhibition of deposition.

What is claimed is:

1. A compound of the formula I

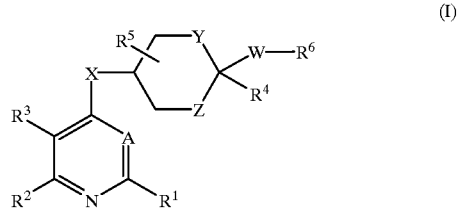

in which

R$^1$ is hydrogen, fluorine or chlorine

R$^2$ and R$^3$ independently of one another are hydrogen, (C$_1$–C$_4$)-alkyl, (C$_1$–C$_4$)-haloalkyl, (C$_2$–C$_4$)-alkenyl, (C$_2$–C$_4$)-haloalkenyl, (C$_2$–C$_4$)-alkynyl, (C$_2$–C$_4$)-haloalkynyl, tri-(C$_1$–C$_4$)-alkylsilyl-(C$_2$–C$_4$)-alkynyl, (C$_1$–C$_4$)-alkoxy, (C$_1$–C$_4$)-haloalkoxy, (C$_1$–C$_4$)-alkoxy-(C$_1$–C$_4$)-alkyl, (C$_1$–C$_4$)-haloalkoxy-(C$_1$–C$_4$)-alkyl, (C$_1$–C$_4$)-alkoxy-(C$_1$–C$_4$)-haloalkyl, (C$_1$–C$_4$)-haloalkoxy-(C$_1$–C$_4$)-haloalkyl, halogen, hydroxyl, (C$_1$–C$_4$)-hydroxyalkyl, (C$_1$–C$_4$)-alkanoyl, (C$_1$–C$_4$)-alkanoyl-(C$_1$–C$_4$)-alkyl, (C$_2$–C$_4$)-haloalkanoyl, (C$_3$–C$_5$)-cycloalkyl, (C$_3$–C$_5$)-halocycloalkyl, (C$_4$–C$_5$)-cycloalkenyl, (C$_4$–C$_5$)-halocycloalkenyl, (C$_3$–C$_5$)-cycloalkoxy, cyano, cyan-(C$_1$–C$_4$)-alkyl, nitro, nitro-(C$_1$–C$_4$)-alkyl, thiocyano, thiocyano-(C$_1$–C$_4$)-alkyl, (C$_1$–C$_4$)-alkoxycarbonyl, (C$_1$–C$_4$)-alkoxycarbonyl-(C$_1$–C$_4$)-alkyl, (C$_1$–C$_4$)-haloalkoxycarbonyl, (C$_1$–C$_4$)-alkylthio, (C$_1$–C$_4$)-haloalkylthio, (C$_1$–C$_4$)-alkylthio-(C$_1$–C$_4$)-alkyl, (C$_1$–C$_4$)-haloalkylthio-(C$_1$–C$_4$)-alkyl, (C$_1$–C$_4$)alkylthio-(C$_1$–C$_4$)-haloalkyl, (C$_1$–C$_4$)-alkylsulfmyl, (C$_1$–C$_4$)-haloalkylsulfinyl, (C$_1$–C$_4$)-alkylsulfonyl, (C$_1$–C$_4$)-haloalkylsulfonyl; or R$^2$ and R$^3$ together with the carbon atoms to which they are bonded form an unsaturated 5- or 6-member carbocyclic ring which, it is a 5-membered ring, a CH$_2$ is optionally replaced by an oxygen or sulfur atom or which, if it is a 6-membered ring, one or two CH units is optionally replaced by a nitrogen atom, and which is optionally substituted by 1, 2 or 3 identical or different radicals and these radicals are (C$_1$–C$_4$)-alkyl, (C$_1$–C$_4$)-haloalkyl, halogen, (C$_1$–C$_4$)-alkoxy or (C$_1$–C$_4$)-haloalkoxy; or R$^2$ and R$^3$ together with the carbon atoms to which they are bonded form a saturated 5-, 6- or 7- membered carbocyclic ring in which on CH$_2$-group is optionally replaced by oxygen or sulfur and which is optionally substituted by 1, 2 or 3 (C$_1$–C$_4$)-alkyl groups;

A is N;

X is NH, oxygen or S(O)$_q$ where q=0, 1 or 2;

Y is a direct bond or CH$_2$;

Z is oxygen or sulfur;

R$^4$, R$^5$ and W-R$^6$ are substituents of the heteroaliphatic ring system, where R$^4$ and R$^5$ independently of one another are hydrogen, halogen, cyano, (C$_1$–C$_4$)-alkyl, (C$_1$–C$_4$)-haloalkyl, (C$_2$–C$_4$)-alkenyl, (C$_2$–C$_4$)-haloalkenyl, (C$_2$–C$_4$)-alkynyl, (C$_2$–C$_4$)-haloalkynyl, (C$_3$–C$_6$)-cycloalkyl, (C$_4$–C$_6$)-Cycloalkenyl, (C$_1$–C$_4$)-alkoxy, (C$_1$–C$_4$)-haloalkoxy, (C$_1$–C$_4$)-alkanoyloxy, (C$_1$–C$_4$)- haloalkanoyloxy, $(C_1-C_4)$-alkylthio or $(C_1-C_4)$-haloalkylthio;

W is a direct bond, oxygen, —$NR^{12}$—, —CO—, —COO—, $CONR^{12}$—, sulfur, —C=N—, —C=N—O— or —$NR^{12}$O—;

$R^6$ is alkyl, alkenyl, alkynyl, cycloalkyl or cycloalkenyl wherein the last-mentioned 5 radicals are optionally substituted by one or more, in the case of fluorine up to the maximum number of, identical or different radicals $D^1R^{16}$, or $R^6$ is aryl which is unsubstituted or substituted by up to three, in the case of fluorine also up to the maximum number of, identical or different radicals $D^2R^{17}$, or $R^4$ and $R^6$ together form a three- to eight-membered ring system which is linked spirocyclically to the ring system containing Y and Z and in which one $CH_2$ group in the ring formed by $R^4$ and $R^6$ is optionally replaced by hetero atom units selected from the group consisting of oxygen, $S(O)_n$ where n=0, 1 or 2, or $NR^{18}$ where $R^{12}$ is hydrogen, $(C_1-C_4)$-alkyl, $(C_1-C_4)$-alkanoyl or $(C_3-C_5)$-cycloalkyl;

$R^{18}$ is hydrogen, alkyl, alkanoyl, alkoxy, benzyl, or aryl, wherein the last-mentioned 2 radicals are unsubstituted substituted with up to three, in the case of fluorine also up to the maximum number of, identical or different substituents $R^{19}$;

$R^{19}$ is $(C_1-C_4)$-alkyl, $(C_1-C_4)$-haloalkyl, $(C_1-C_4)$-alkoxy, $(C_1-C_4)$-haloalkoxy, cyano, nitro or halogen, and the ring system formed by $R^4$ and $R^6$ is unsubstituted or substituted with up to three substituents $D^3R^{20}$, or the ring system formed by $R^4$ and $R^6$ together with a fither benzene ring or cyclohexane ring forms a fused ring system and the benzene ring in these fused systems are unsubstituted or substituted with up to three, in the case of fluorine also up to the maximum number of, identical or different substituents $D^4R^{21}$, where $D^1$, $D^2$, $D^3$ and $D^4$ are in each case independent of one another and are a direct bond, oxygen, $S(O)_k$, $SO_2O$, $OSO_2$, CO, OCO, COO, $SO_2NR^{22}$, $NR^{22}SO_2$, $NR^{22}O$, $ONR^{22}$, $NR^{22}$, $NR^{22}CO$, $CONR^{22}$ or $SiR^{23}R^{24}$, where k is 0, 1 or 2; and $R^{16}$, $R^{17}$, $R^{20}$ and $R^{21}$ in each case independently of one another are hydrogen, cyano, nitro, halogen, $(C_1-C_8)$-alkyl, $(C_1-C_8)$-haloalkyl, $(C_2-C_8)$-alkenyl, $(C_2-C_8)$-haloalkenyl, $(C_2-C_8)$alkynyl, $(C_2-C_8)$-haloalkynyl, $(C_1-C_8)$-alkoxy$(C_1-C_4)$-alkyl, $(C_1-C_8)$-haloalkoxy$(C_1-C_4)$-alkyl, $(C_1-C_8)$-alkylthio$(C_1-C_4)$-alkyl, $(C_1-C_8)$-haloalkylthio $(C_1-C_4)$-alkyl, $(C_3-C_8)$-cycloalkyl, $(C_4-C_8)$-cycloalkenyl, $(C_3-C_8)$-cycloalkyl-$(C_1-C_4)$-alkyl, $(C_4-C_8)$-cycloalkenyl-$(C_1-C_4)$-alkyl, aryl or aryl-$(C_1-C_4)$-alkyl wherein the cycloaliphatic or aromatic ring systems in the last-mentioned 6 radicals are unsubstituted or substituted with up to three, in the case of fluorine also up to the maximum number of, identical or different substituents $R^{25}$, where $R^{22}$ radicals independently of one another are hydrogen, $(C_1-C_4)$-alkyl, $(C_1-C_4)$-alkanoyl or $(C_3-C_5)$-cycloalkyl and $R^{23}$ and $R^{24}$ independently of one another are $(C_1-C_4)$-alkyl and $R^{25}$ radicals independently of one another are $(C_1-C_4)$-alkyl, $(C_1-C_4)$-haloalkyl, $(C_1-C_4)$-alkoxy, $(C_1-C_4)$-haloalkoxy, cyano, nitro, halogen, $(C_1-C_4)$-alkanoyl or $(C_2-C_4)$-haloalkanoyl, or two of the radicals $R^{16}$, $R^{17}$, $R^{20}$, $R^{21}$, $R^{25}$ on the same carbon atom together and in each case independently of one another are an oxo group;

or a salt thereof.

2. A compound of the formula I as claimed in claim 1 where $R^2$ and $R^3$ independently of one another are hydrogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, tri-$(C_1-C_4)$-alkylsilyl-$(C_2-C_4)$-alkynyl, $(C_1-C_4)$-alkoxy, $(C_1-C_4)$-haloalkoxy, $(C_1-C_4)$-alkoxy-$(C_1-C_4)$-alkyl, $(C_1-C_4)$haloalkoxy-$(C_1-C_4)$-alkyl, $(C_1-C_4)$-alkoxy-$(C_1-C_4)$-haloalkyl, $(C_1-C_4)$-haloalkoxy-$(C_1-C_4)$-haloalkyl, halogen, hydroxyl, $(C_1-C_4)$-hydroxyalkyl, $(C_1-C_4)$-alkanoyl, $(C_1-C_4)$-alkanoyl-$(C_1-C_4)$-alkyl, $(C_2-C_4)$-haloalkanoyl, $(C_3-C_5)$-cycloalkyl, $(C_3-C_5)$-halocycloalkyl, $(C_4-C_5)$-cycloalkenyl, $(C_4-C_5)$-halocycloalkenyl, $(C_3-C_5)$-cycloalkoxy, cyano, cyan-$(C_1-C_4)$-alkyl, nitro, nitro-$(C_1-C_4)$-alkyl, thiocyano, thiocyano-$(C_1-C_4)$-alkyl, $(C_1-C_4)$-alkoxycarbonyl, $(c_1-C_4)$alkoxycarbonyl-$(C_1-C_4)$-alkyl, $(C_1-C_4)$-haloalkoxycarbonyl, $(C_1-C_4)$-alkylthio, $(C_1-C_4)$-haloalkylthio, $(C_1-C_4)$-alkylthio-$(C_1-C_4)$-alkyl, $(C_1-C_4)$haloalkylthio-$(C_1-C_4)$-alkyl, $(C_1-C_4)$-alkylthio-$(C_1-C_4)$-haloalkyl, $(C_1-C_4)$-alkylsulfinyl, $(C_1-C_4)$-haloalkylsulfinyl, $(C_1-C_4)$-alkylsulfonyl, $(C_1-C_4)$-haloalkylsulfonyl; or $R^2$ and $R^3$ together with the carbon atoms to which they are bonded form an unsaturated 5- or 6-membered carbocyclic ring which, if it is a 5-membered ring, one or two $CH_2$ units are optionally replaced by one or two nitrogen atoms, and which is optionally substituted by 1, 2 or 3 identical or different radicals and these radicals are $(C_1-C_4)$-alkyl, trifluoromethyl, halogen, $(C_1-C_4)$-alkoxy or $(C_1-C_4)$-haloalkoxy; or $R^2$ and $R^3$ together with the carbon atoms to which they are bonded form a saturated 5-, 6- or 7-membered carbocyclic ring in which one $CH_2$ is optionally replaced by an oxygen or sulfur atom, and which is optionally substituted by 1, 2 or 3 $(C_1-C_4)$-alkyl groups;

$R^4$, $R^5$ and W-$R^6$ are substituents of the heteroaliphatic ring system, where $R^4$ and $R^5$ independently of one another are hydrogen, halogen, cyano, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_3-C_6)$-cycloalkyl, $(C_4-C_6)$-cycloalkenyl, $(C_1-C_4)$-alkoxy, $(C_1-C_4)$-haloalkoxy, $(C_1-C_4)$-alkanoyloxy, $(C_1-C_4)$-haloalkanoyloxy, $(C_1-C_4)$-alkylthio or $(C_1-C_4)$-haloalkylthio;

W is a direct bond, oxygen, —$NR^{12}$—, —CO—, —COO—, $CONR^{12}$—, sulflur, —C=N—, —C=N—O— or —$NR^{12}$O—;

$R^6$ is alkyl, alkenyl, alkynyl, cycloalkyl or cycloalkenyl and wherein these last-mentioned 5 radicals are optionally substituted by up to three, in the case of fluorine up to the maximum number of, identical or different radicals $D^1R^{16}$, or $R^6$ is aryl which is unsubstituted or substituted by up to three, in the case of fluorine also up to the maximum number of, identical or different radicals $D^2R^{17}$, or $R^4$ and $R^6$ together form a three- to eight-membered ring system which is linked spirocyclically to the ring system containing Y and Z and in which one $CH_2$ group in the ring formed by $R^4$ and $R^6$ is optionally replaced by hetero atom units selected from the group consisting of oxygen, $S(O)_n$ where n=0, 1 or 2, or $NR^{18}$, where $R^{12}$ is hydrogen, $(C_1–C_4)$-alkyl, $(C_1–C_4)$-alkanoyl or $(C_3–C_5)$-cycloalkyl;

$R^{18}$ is hydrogen, alkyl, alkanoyl, alkoxy, benzyl, or aryl wherein the last-mentioned 2 radicals are unsubstituted or substituted with up to three, in the case of fluorine also up to the maximum number of, identical or different substituents $R^{19}$, $R^{19}$ is $(C_1–C_4)$-alkyl, $(C_1–C_4)$-haloalkyl, $(C_1–C_4)$-alkoxy, $(C_1–C_4)$-haloalkoxy, cyano, nitro or halogen, and the ring system formed by $R^4$ and $R^6$ can be unsubstituted or provided with one substituent, $D^3R^3$, or the ring system formed by $R^4$ and $R^6$ together with a further benzene ring or cyclohexane ring forms the indane, 1,2,3,4-tetrahydronaphthalene, decalin or benzocycloheptane system, and the benzene ring in these fised systems is unsubstituted or substituted with up to three, in the case of fluorine also up to the maximwn number of, identical or different substituents $D^4R^{21}$, where $D^1$, $D^2$, $D^3$ and $D^4$ are in each case independent of one another and are a direct bond, oxygen, $S(O)_k$, $SO_2O$, $OSO_2$, CO, OCO, COO, $SO_2NR^{22}$, $NR^{22}SO_2$, $NR^{22}O$, $ONR^{22}$, $NR^{22}$, $NR^{22}CO$, $CONR^{22}$ or $SiR^{23}R^{24}$, where k is 0, 1 or 2; and $R^{16}$, $R^{17}$, $R^{20}$ and $R^{21}$ in each case independently of one another are hydrogen, cyano, nitro, halogen, $(C_1–C_8)$-alkyl, $(C_1–C_8)$-haloalkyl, $(C_2–C_8)$-alkenyl, $(C_2–C_8)$-haloalkenyl, $(C_2–C_8)$alkynyl, $(C_2–C_8)$-haloalkynyl, $(C_1–C_8)$-alkoxy$(C_1–C_4)$-alkyl, $(C_1–C_8)$-haloalkoxy $(C_1–C_4)$-alkyl, $(C_1–C_8)$-alkylthio$(C_1–C_4)$-alkyl, $(C_1–C_8)$-haloalkylthio $(C_1–C_4)$-alkyl, $(C_3–C_8)$-cycloalkyl, $(C_4–C_8)$-cycloalkenyl, $(C_3–C_8)$-cycloalkyl-$(C_1–C_4)$-alkyl, $(C_4–C_8)$-cycloalkenyl-$(C_1–C_4)$-alkyl, aryl, or aryl-$(C_1–C_4)$-alkyl wherein the cycloaliphatic or aromatic ring systems in the last-mentioned 6 radicals are unsubstituted or substituted with up to three, in the case of fluorine also up to the maximum number of, identical or different substituents $R^{25}$, where $R^{22}$ radicals independently of one another are hydrogen, $(C_1–C_4)$-alkyl, $(C_1–C_4)$-alkanoyl or $(C_3–C_5)$-cycloalkyl and $R^{23}$ and $R^{24}$ independently of one another are $(C_1–C_4)$-alkyl and $R^{25}$ radicals independently of one another are $(C_1–C_4)$-alkyl, $(C_1–C_4)$-haloalkyl, $(C_1–C_4)$-alkoxy, $(C_1–C_4)$-haloalkoxy, cyano, nitro, halogen, $(C_1–C_4)$-alkanoyl or $(C_2–C_4)$-haloalkanoyl, or two of the radicals $R^{16}$, $R^{17}$, $R^{20}$, $R^{21}$, $R^{25}$ on the same carbon atom together and in each case independently of one another are an oxo group or an acid addition salt thereof.

3. A compound of the formula I as claimed in claim 1 where $R^1$ is hydrogen, chlorine or fluorine, $R^2$ is $(C_1–C_4)$-alkyl, $(C_2–C_4)$-alkenyl, $(C_2–C_4)$-alkynyl, tri-$(C_1–C_4)$-alkylsilyl-$(C_2–C_4)$-alkynyl, $(C_1–C_4)$-haloalkyl, cyclopropyl, halocyclopropyl, methoxymethyl or cyano;

$R^3$ is hydrogen, halogen, methyl, ethyl, ethenyl, ethynyl, methoxy, ethoxy, cyano, trifluoromethyl, fluoromethylthio or methoxycarbonyl; or $R^2$ and $R^3$ together with the carbon atoms to which they are bonded form an unsaturated 5- or 6-membered carbocyclic ring which, if it is a 5-membered ring, a $CH_2$ is optionally replaced by a sulfur atom and which is optionally substituted by 1, 2, or 3 identical or different radicals and these radicals are $(C_1–C_4)$-alkoxy or $(C_1–C_4)$-haloalkoxy; or $R^2$ and $R^3$ together with the carbon atoms to which they are bonded form a saturated 5- or 6-membered ring in which one CH group is optionally replaced by sulfur;

A is N;

X is NH or oxygen;

Y is a direct bond or $CH_2$;

Z is oxygen or sulfur;

$R^4$ is hydrogen, $(C_1–C_4)$-alkyl, trifluoromethyl or $(C_1–C_4)$-alkoxy;

$R^5$ is hydrogen; and

W is a direct bond, oxygen, —CO—, —COO—, $CONR^{12}$, sulfur, —C=N—, —C=N—O— and $R^{12}$ is hydrogen, $(C_1–C_4)$-alkyl, $(C_1–C_4)$-alkanoyl or $(C_3–C_5)$-cycloalkyl.

4. A compound of the formula I as claimed in claim 1 where $R^1$ is hydrogen, $R^2$ is methyl, ethyl, propyl, isopropyl, $(C_1–C_2)$-fluoroalkyl, cyclopropyl or methoxymethyl;

$R^3$ is halogen, methyl, ethyl, ethenyl, ethynyl, methoxy, ethoxy, trifluoromethyl, fluoromethylthio, methoxycarbonyl or cyano; or $R^2$ and $R^3$ together with the ring system to which they are bonded form the quinazoline system which is optionally substituted by fluorine in the carbocyclic moiety; or $R^2$ and $R^3$ together with the carbon atoms to which they are bonded form a saturated 6-membered ring in which one $CH_2$ group is optionally replaced by an oxygen or sulfur atom;

$R^4$ is hydrogen or methyl; and $R^5$ is hydrogen.

5. An insecticidal composition comprising an insecticidally active amount of one or more of a compound as claimed in claim 1 together with one or more of an additive or auxiliary.

6. A compound of the formula I as claimed in claim 1 where $R^6$ is $(C_1–C_{20})$-alkyl, $(C_2–C_{20})$-alkenyl, $(C_2–C_{20})$-alkynyl, $(C_3–C_8)$-cycloalkyl or $(C_4–C_8)$-cycloalkenyl, and where these last-mentioned 5 radicals, can optionally be substituted by up to three, in the case of fluorine up to the maximum number of, identical or different radicals $D^1R^{16}$, or $R^6$ is aryl which is unsubstituted or substituted by up to three, in the case of fluorine also up to the maximum number of, identical or different radicals $D^2R^{17}$, or $R^4$ and $R^6$ together form a three- to eight-membered ring system which is spirocyclically linked with the ring system containing Y and Z and in which one $CH_2$ group in the ring formed by $R^4$ and $R^6$ is optionally replaced by hetero atom units selected from the group consisting of oxygen, $S(O)_n$ where n=0, 1 or 2 or $NR^{18}$, $R^{18}$ is hydrogen, $(C_1–C_8)$-alkyl, $(C_1–C_8)$-alkanoyl, $(C_1–C_8)$-alkoxy, benzoyl, or aryl, wherein the last-mentioned 2 radicals to be unsubstituted or substituted with up to three, in the case of fluorine also up to the maximum number of, identical or different substituents $R^{19}$;

$R^{19}$ is $(C_1–C_4)$-alkyl, $(C_1–C_4)$-haloalkyl, $(C_1–C_4)$-alkoxy, $(C_1–C_4)$-haloalkoxy, cyano, nitro or halogen, and the ring system formed by $R^4$ and $R^6$ can be unsubstituted or provided with one substituent, $D^3R^{20}$, or the ring system formed by $R^4$ and $R^6$ together with a further benzene ring or cyclohexane ring forms the indane, 1,2,3,4-tetrahydronaphthalene, decalin or benzocycloheptane system, and the benzene ring in these fused systems is unsubstituted or substituted with up to three, in the case of fluorine also up to the maximum number of, identical or different substituents $D^4R^{21}$, where, amongst the compounds for which the carbon atom between Y and Z only has attached to it the substituent $W$-$R^6$, the substituents X and $W$-$R^6$ are in the cis-position relative to each other;

$D^1$, $D^2$, $D^3$ and $D^4$ are in each case independent of one another and are a direct bond, oxygen, $S(O)_k$, $SO_2O$, $OSO_2$, $CO$, $OCO$, $COO$, $SO_2NR^{22}$, $NR^{22}SO_2$, $ONR^{22}$, $NR^{22}O$, $SiR^{23}O$, $NR^{22}CO$, $CONR^{22}$ or $SiR^{23}R^{24}$, where k is 0, 1 or 2; and $R^{16}$, $R^{17}$, $R^{20}$ and $R^{21}$ in each case independently of one another are hydrogen, cyano, nitro, halogen, $(C_1-C_8)$-alkyl, $(C_1-C_8)$-haloalkyl, $(C_2-C_8)$-alkenyl, $(C_2-C_8)$-haloalkenyl, $(C_2-C_8)$alkynyl, $(C_2-C_8)$-haloalkynyl, $(C_1-C_8)$-alkoxy$(C_1-C_4)$-alkyl, $(C_1-C_8)$-haloalkoxy $(C_1-C_4)$-alkyl, $(C_1-C_8)$-alkylthio$(C_1-C_4)$-alkyl, $(C_1-C_8)$-haloalkylthio$(C_1-C_4)$-alkyl, $(C_3-C_8)$-cycloalkyl, $(C_4-C_8)$-cycloalkenyl, $(C_3-C_8)$-cycloalkyl-$(C_1-C_4)$-alkyl, $(C_4-C_8)$-cycloalkenyl-$(C_1-C_4)$-alkyl, aryl or aryl-$(C_1-C_4)$-alkyl wherein the cycloaliphatic, aromatic or heterocyclic ring systems in the last-mentioned 6 radicals are unsubstituted or substituted with up to three, in the case of fluorine also up to the maximum number of, identical or different substituents $R^{25}$;

$R^{22}$ radicals independently of one another are hydrogen, $(C_1-C_4)$-alkyl, $(C_1-C_4)$-alkanoyl or $(C_3-C_5)$-cycloalkyl and $R^{23}$ and $R^{24}$ independently of one another are $(C_1-C_4)$-alkyl and $R^{25}$ radicals independently of one another are $(C_1-C_4)$-alkyl, $(C_1-C_4)$-haloalkyl, $(C_1-C_4)$-alkoxy, $(C_1-C_4)$-haloalkoxy, cyano, nitro, halogen, $(C_1-C_4)$-alkanoyl or $(C_2-C_4)$-haloalkanoyl, or two of the radicals $R^{16}$, $R^{17}$, $R^{20}$, $R^{21}$, $R^{25}$ on the same carbon atom together and in each case independently of one another are an oxo group.

7. A compound of the formula I as claimed in claim 1 where $R^6$ is $(C_1-C_8)$-alkyl, $(C_2-C_8)$-alkenyl, $(C_2-C_8)$-alkynyl, $(C_3-C_8)$-cycloalkyl or $(C_4-C_8)$-cycloalkenyl and where these last mentioned 5 radicals optionally is substituted by up to three, in the case of fluorine up to the maximum number of, identical or different radicals $D^1R^{16}$, or $R^6$ is aryl which is unsubstituted or substituted by up to three, in the case of fluorine also up to the maximum number of identical or different radicals $D^2R^{17}$, or $R^4$ and $R^6$ together form a five- or six-membered ring system which is spirocyclically linked to the ring system containing Y and Z and in which one $CH_2$ group in the ring formed by $R^4$ and $R^6$ is optionally replaced by hetero atom units selected from the group consisting of oxygen, $S(O)_n$ where n=0, 1 or 2 or $NR^{18}$, where $R^{18}$ is hydrogen, $(C_1-C_8)$-alkyl, $(C_1-C_8)$-alkanoyl, alkoxy, benzoyl, or aryl wherein the last-mentioned 2 radicals are unsubstituted or substituted with up to three, in the case of fluorine also up to the maximum number of, identical or different substituents $R^{19}$, and $R^{19}$ is $(C_1-C_4)$-alkyl, $(C_1-C_4)$-haloalkyl, $(C_1-C_4)$-alkoxy, $(C_1-C_4)$-haloalkoxy, cyano, nitro or halogen, and the ring system formed by $R^4$ and $R^6$ can be unsubstituted or provided with one substituent, $D^3R^{20}$, or the ring system formed by $R^4$ and $R^6$ together with a further benzene ring or cyclohexane ring forms the indane, 1,2,3,4-tetrahydronaphthalene, decalin or benzocycloheptane system, and the benzene ring in these fised systems is unsubstituted or provided with up to three, in the case of fluorine also up to the maximum number of, identical or different substituents $D^4R^{21}$, where, amongst the compounds for which the carbon atom between Y and Z where Y=$CH_2$ only has attached to it the substituent W-$R^6$, the substituents X and W-$R^6$ are in the cis-position relative to each other;

$D^1$, $D^2$, $D^3$ and $D^4$ are in each case independent of one another and are a direct bond, oxygen, $S(O)_k$, $SO_2O$, $OSO_2$, $CO$, $OCO$, $COO$, $SO_2NR^{22}$, $NR^{22}SO_2$, $NR^{22}O$, $ONR^{22}$, $NR^{22}$, $NR^{22}CO$ or $CONR^{22}$, where k is 0, 1 or 2; and $R^{22}$ radicals independently of one another are hydrogen, $(C_1-C_4)$-alkyl, $(C_1-C_4)$-alkanoyl or $(C_3-C_5)$-cycloalkyl, and where $R^{16}$, $R^{17}$, $R^{20}$ and $R^{21}$ in each case independently of one another are hydrogen, cyano, nitro, halogen, $(C_1-C_8)$-alkyl, $(C_3-C_8)$-cycloalkyl, or aryl, where the cycloaliphatic or aromatic in the last-mentioned 2 radicals are unsubstituted or substituted with up to three, in the case of fluorine also up to the maximum number of, identical or different substitutents $R^{25}$, where $R^{25}$ radicals independently of one another are $(C_1-C_4)$-alkyl, $(C_1-C_4)$haloalkyl, $(C_1-C_4)$-alkoxy, $(C_1-C_4)$-haloalkoxy, cyano, nitro, halogen, or two of the radicals $R^{16}$, $R^{17}$, $R^{20}$, $R^{21}$, and $R^{25}$ on the same carbon atom together and in each case independently of one another are an oxo group.

8. A compound of the formula I as claimed in claim 1 where $R^6$ is $(C_1-C_8)$-alkyl is optionally substituted by up to three, in the case of fluorine up to the maximum number of, identical or different radicals $D^1R^{20}$, or $R^6$ is aryl which is unsubstituted or to be substituted by up to three, in the case of fluorine also up to the maximum number of, identical or different radicals $D^2R^{21}$.

9. A compound of the formula I as claimed in claim 1 where $R^1$ is hydrogen;

$R^2$ is ethyl, propyl, isopropyl, 1-fluoroethyl or methoxymethyl;

$R^3$ is fluorine, chlorine, bromine, cyano, ethenyl, ethynyl or methoxy; or, $R^2$ and $R^3$ together with the ring system to which they are bonded form the quinazoline system which can be substituted by a fluorine atom;

$R^4$ is hydrogen or methyl; and $R^5$ is hydrogen.

10. A compound of the formula I as claimed in claim 1 where $R^1$ is hydrogen;

$R^2$ is ethyl or methoxymethyl;

$R^3$ is fluorine, chlorine, bromine or methoxy; or

X is NH;

Z is oxygen and $R^4$ and $R^5$ are hydrogen.

11. A method for controlling insects or their eggs, which comprises applying to said insects or their eggs or to plants, areas or substrates infested with them, an insecticidally active amount of a compound as claimed in claim 1.

* * * * *